(12) United States Patent
Honda et al.

(10) Patent No.: US 10,149,911 B2
(45) Date of Patent: Dec. 11, 2018

(54) PHARMACEUTICAL COMPOSITION CONTAINING HYDROXAMIC ACID DERIVATIVE OR SALT THEREOF

(71) Applicant: TOYAMA CHEMICAL CO., LTD., Shinjuku-ku (JP)

(72) Inventors: Tatsuya Honda, Toyama (JP); Yuko Suzumura, Toyama (JP); Tomoya Kato, Toyama (JP); Yu Koseki, Toyama (JP); Kohei Ono, Toyama (JP)

(73) Assignee: TOYAMA CHEMICAL CO., LTD., Shinjuku-ku (JP)

( * ) Notice: Subject to any disclaimer, the term of this patent is extended or adjusted under 35 U.S.C. 154(b) by 0 days.

(21) Appl. No.: 15/510,487

(22) PCT Filed: Sep. 11, 2015

(86) PCT No.: PCT/JP2015/075779
§ 371 (c)(1),
(2) Date: Mar. 10, 2017

(87) PCT Pub. No.: WO2016/039433
PCT Pub. Date: Mar. 17, 2016

(65) Prior Publication Data
US 2017/0290918 A1    Oct. 12, 2017

(30) Foreign Application Priority Data

Sep. 12, 2014 (JP) ................................. 2014-186570
May 28, 2015 (JP) ................................. 2015-108356

(51) Int. Cl.
| | | |
|---|---|---|
| A61K 47/40 | (2006.01) | |
| A61K 9/08 | (2006.01) | |
| A61K 9/19 | (2006.01) | |
| A61K 31/16 | (2006.01) | |
| A61K 9/00 | (2006.01) | |
| A61K 31/166 | (2006.01) | |

(52) U.S. Cl.
CPC ............ *A61K 47/40* (2013.01); *A61K 9/0019* (2013.01); *A61K 9/08* (2013.01); *A61K 9/19* (2013.01); *A61K 31/16* (2013.01); *A61K 31/166* (2013.01)

(58) Field of Classification Search
CPC ...................................................... A61K 47/40
See application file for complete search history.

(56) References Cited

U.S. PATENT DOCUMENTS

| | | |
|---|---|---|
| 2010/0008923 A1 | 1/2010 | Shultz |
| 2013/0072677 A1 | 3/2013 | Takashima et al. |
| 2016/0039751 A1* | 2/2016 | Shoji ..................... C07D 309/12 549/510 |

FOREIGN PATENT DOCUMENTS

| | | |
|---|---|---|
| EP | 2 975 022 A1 | 1/2016 |
| JP | 2009-541488 A | 11/2009 |
| WO | 2004/062601 A2 | 7/2004 |
| WO | 2007/069020 A2 | 6/2007 |
| WO | 2008/105515 A1 | 9/2008 |
| WO | 2008/154642 A2 | 12/2008 |
| WO | 2008/154642 A3 | 12/2008 |
| WO | 2010/017060 A1 | 2/2010 |
| WO | 2010/024356 A1 | 3/2010 |
| WO | 2010/031750 A1 | 3/2010 |
| WO | 2010/032147 A2 | 3/2010 |
| WO | 2011/132712 A1 | 10/2011 |
| WO | WO 2013/170165 A1 | 11/2013 |
| WO | 2014/142298 A1 | 9/2014 |
| WO | 2015/056799 A1 | 4/2015 |
| WO | 2015/056800 A1 | 4/2015 |

OTHER PUBLICATIONS

International Search Report dated Nov. 17, 2015, in PCT/JP2015/075779, filed Sep. 11, 2015.
Livermore, "Multiple Mechanisms of Antimicrobial Resistance in *Pseudomonas aeruginosa:* Our Worst Nightmare?", Antimicrobial Resistance, Mar. 1, 2002, p. 634-640.
Van Eldere, "Multicentre surveillance of Pseudomonas aeruginosa susceptibility patterns in nosocomial infections", Journal of Antimicrobial Chemotherapy, vol. 51, 2003, 7 pages.
Mikamo, et al., Surveillance on Pseudomonas aeruginosa Isolated in Gifu Prefecture (2004), The Japanese Journal of Antibiotics, vol. 59, No. 5, Oct. 2006, 9 pages (with partial English translation).
Young, et al., "The envA Permeability/Cell Division Gene of *Escherichia coli* Encodes the Second Enzyme of Lipid A Biosynthesis", Journal of Biological Chemistry, vol. 270, No. 51, 1995, (total 9 pages).
Beall, et al., "Sequence Analysis, Transcriptional Organization, and Insertional Mutagenesis of the envA Gene of *Escherichia coli*", Journal of Bacteriology, vol. 169, No. 12, Dec. 1987, p. 5408-5415.
Kurkov, et al., "Cyclodextrins", International Journal of Pharmaceutics, vol. 453, 2013, p. 167-180.
Uekama, "Novel Approach of Cyclodextrin-based Pharmaceutical Formulation", Yakugaku Zasshi, vol. 132, No. 1, p. 85-105 (with partial English translation).
Extended European Search Report dated Mar. 16, 2018 in Patent Application No. 15840105.9, 7 pages.

* cited by examiner

*Primary Examiner* — Shawquia Jackson
(74) *Attorney, Agent, or Firm* — Oblon, McClelland, Maier & Neustadt, L.L.P.

(57) ABSTRACT

This pharmaceutical composition contains a hydroxamic acid derivative, or a salt thereof, and a solubilizer, said hydroxamic acid derivative being selected from among (2S)-2-((4-((4-((1S)-1,2-dihydroxyethyl)phenyl)ethynyl) benzoyl)(methyl)amino)-N-hydroxy-N',2-dimethylmalonamide, 2S)-2-((4-((4-((1R)-1,2-dihydroxyethyl)phenyl)ethynyl)benzoyl)(methyl)amino)-N-hydroxy-N',2-dimethylmalonamide, and (2S)-N-hydroxy-2-((4-((4-((1S)-1-hydroxy-2-methoxyethyl)phenyl)ethynyl)benzoyl) (methyl)amino)-N',2-dimethylmalonamide. The pharmaceutical composition demonstrates strong antibacterial activity, has excellent solubility in water, and is useful as a drug.

16 Claims, No Drawings

PHARMACEUTICAL COMPOSITION CONTAINING HYDROXAMIC ACID DERIVATIVE OR SALT THEREOF

TECHNICAL FIELD

The present invention relates to pharmaceutical compositions comprising novel hydroxamic acid derivatives or the salt thereof.

BACKGROUND ART

Gram-negative bacteria have an outer membrane composed of a lipid bilayer, which does not exist in Gram-positive bacteria, and therefore tend to have stronger drug resistance, as compared to Gram-positive bacteria. Gram-negative bacteria are also known to have a plurality of drug efflux proteins, which are involved in drug resistance (Antimicrobial Resistance, 2002, Mar. 1, 34, pp. 634-640).

Among Gram-negative bacteria, *Pseudomonas aeruginosa*, in particular, has a strong tendency to show intrinsic resistance to various antimicrobial drugs. In recent years, *Pseudomonas aeruginosa* which has gained resistance to carbapenem drugs, quinolone drugs, aminoglycoside drugs, or the like has been often isolated in medical settings (J. Antimicrob. Chemother., 2003, Vol. 51, pp. 347-352). Moreover, multi-drug resistant *Pseudomonas aeruginosa* has been isolated (Jpn. J. Antibiotics, 2006, Vol. 59, No. 5, pp. 355-363) and has posed worldwide major problems.

UDP-3-O-acyl-N-acetylglucosamine deacetylase (LpxC) is an enzyme in charge of the synthesis of lipid A (the hydrophobic anchor of LPS, which is the constituent of the outer membrane).

Lipid A biosynthesis consists of reactions in 10 stages, and LpxC catalyzes the second stage to remove the acetyl group of UDP-3-O-acyl-N-acetylglucosamine (J. Biol. Chem., 1995, Vol. 270, pp. 30384-30391). Lipid A is a component essential for the formation of the outer membrane, and is indispensable for the survival of Gram-negative bacteria (J. Bacteriol., 1987, Vol. 169, pp. 5408-5415). LpxC is one of the rate-determining important enzymes during the process of lipid A biosynthesis, and is an indispensable enzyme for lipid A biosynthesis. Thus, a drug inhibiting the activity of LpxC is highly expected to be capable of becoming an antimicrobial agent effective against Gram-negative bacteria including *Pseudomonas aeruginosa*, particularly against drug resistant *Pseudomonas aeruginosa*, because such a drug has a mechanism of action different from those of conventional drugs.

Compounds having LpxC inhibitory activity have been known so far (Patent Documents 1 to 7).

To provide its medicinal efficacy, a drug is required to dissolve at an absorption site. Thus, when a sparingly water-soluble drug is orally administered, the drug may be insufficiently absorbed from the gastrointestinal tract and have a difficulty in providing its medicinal efficacy. Also, in the case of parenteral administration, particularly intravenous administration, the drug is required to be administered in a dissolved form.

Cyclodextrins (sometimes referred to as "CDs" hereinbelow), or cyclodextrin derivatives (sometimes referred to as "CD derivatives" hereinbelow), are known to be used for solubilizing compounds (International J. Pharmaceutics., 2013, Vol. 453, pp. 167-180; Yakugaku Zasshi, 2012, Vol. 132, No. 1, pp. 85-105).

PRIOR ART DOCUMENTS

Patent Documents

Patent Document 1: International Publication No. WO 04/062601 pamphlet
Patent Document 2: International Publication No. WO 07/069020 pamphlet
Patent Document 3: International Publication No. WO 08/154642 pamphlet
Patent Document 4: International Publication No. WO 10/031750 pamphlet
Patent Document 5: International Publication No. WO 10/017060 pamphlet
Patent Document 6: International Publication No. WO 10/032147 pamphlet
Patent Document 7: International Publication No. WO 11/132712 pamphlet

SUMMARY OF INVENTION

Problem to be Solved by the Invention

An object of the present invention is to provide a pharmaceutical composition that exhibits potent antimicrobial activity against Gram-negative bacteria, including *Pseudomonas aeruginosa* and their drug resistant strains, by inhibiting LpxC, and has excellent water solubility. Another object of the present invention is to provide a method for producing an excellently stable liquid formulation comprising the pharmaceutical composition.

Means for Solving the Problem

Under such circumstances, the present inventors have intensively studied to find that pharmaceutical compositions that contain hydroxamic acid derivatives selected from (2S)-2-((4-((4-((1S)-1,2-dihydroxyethyl)phenyl)ethynyl)benzoyl)(methyl)amino)-N-hydroxy-N',2-dimethylmalonamide (sometimes referred to as "Compound A" hereinbelow), (2S)-2-((4-((4-((1R)-1,2-dihydroxyethyl)phenyl)ethynyl)benzoyl)(methyl)amino)-N-hydroxy-N',2-dimethylmalonamide (sometimes referred to as "Compound B" hereinbelow) and (2S)-N-hydroxy-2-((4-((4-((1S)-1-hydroxy-2-methoxyethyl)phenyl)ethynyl)benzoyl)(methyl)amino)-N',2-dimethylmalonamide (sometimes referred to as "Compound C" hereinbelow), or salts thereof, and a solubilizing agent have potent antimicrobial activity and excellent solubility and are useful as medicines. Additionally, the inventors have found that an excellently stable liquid formulation can be produced by obtaining an aqueous solution of a hydroxamic acid derivative or a salt thereof and a solubilizing agent and then, as required, adjusting the pH of the obtained aqueous solution to 3 to 8, and thereby have completed the present invention.

That is, the present invention provides the following.

[1] A pharmaceutical composition comprising a hydroxamic acid derivative selected from Compound A, Compound B and Compound C, or a salt thereof, and a solubilizing agent.

[2] The pharmaceutical composition according to [1], wherein the solubilizing agent is a CD or a CD derivative.

[3] The pharmaceutical composition according to [1] or [2], wherein the hydroxamic acid derivative is Compound A.

[4] The pharmaceutical composition according to [2] or [3], wherein the CD or the CD derivative is one or more selected from α-cyclodextrin (sometimes referred to as "αCD" hereinbelow), γ-cyclodextrin (sometimes referred to as "γCD" hereinbelow), hydroxypropyl-α-cyclodextrin (sometimes referred to as "HPαCD" hereinbelow), sulfobutylether-β-cyclodextrin (sometimes referred to as "SBEβCD" hereinbelow), 2,3,6-tri-O-methyl-β-cyclodextrin, hydroxyethyl-β-cyclodextrin, hydroxypropyl-β-cyclodextrin (sometimes referred to as "HPβCD" hereinbelow), heptakis-2,6-di-O-methyl-β-cyclodextrin (sometimes referred to as "DMβCD" hereinbelow), 6-O-α-maltosyl-β-cyclodextrin, methyl-β-cyclodextrin and hydroxypropyl-γ-cyclodextrin (sometimes referred to as "HPγCD" hereinbelow).

[5] The pharmaceutical composition according to [2] or [3], wherein the CD or the CD derivative is one or more selected from αCD, γCD, HPαCD, SBEβCD, HPβCD and HPγCD.

[6] The pharmaceutical composition according to any one of [1] to [5], wherein the pharmaceutical composition is a liquid formulation.

[7] The pharmaceutical composition according to [6], wherein a pH of the liquid formulation is from 3 to 8.

[8] The pharmaceutical composition according to any one of [1] to [5], wherein the pharmaceutical composition is a frozen liquid formulation.

[9] The pharmaceutical composition according to [8], wherein a pH of the frozen liquid formulation when thawed is from 3 to 8.

[10] The pharmaceutical composition according to any one of [1] to [5], wherein the pharmaceutical composition is a lyophilized formulation.

[11] The pharmaceutical composition according to [10], wherein a pH of an aqueous solution of the lyophilized formulation is from 3 to 8.

[12] The pharmaceutical composition according to [1], wherein the solubilizing agent is one or more selected from monoalcohols, polyhydric alcohols, amides, sulfoxides, amino acids, surfactants, acids and bases.

[13] The pharmaceutical composition according to [12], wherein the hydroxamic acid derivative is Compound A.

[14] The pharmaceutical composition according to [12] or [13], wherein the monoalcohol is an alcohol having 1 to 6 carbon atoms; the polyhydric alcohol is a diol; and the acid is an organic acid.

[15] The pharmaceutical composition according to [12] or [13], wherein the solubilizing agent is one or more selected from alcohols having 1 to 6 carbon atoms, diols, amino acids and organic acids in combination with an amide.

[16] The pharmaceutical composition according to any one of [12] to [15], wherein the pharmaceutical composition is a liquid formulation.

[17] The pharmaceutical composition according to any one of [1] to [16], wherein the pharmaceutical composition is a pharmaceutical composition used as an LpxC inhibitor.

[18] The pharmaceutical composition according to any one of [1] to [16], wherein the pharmaceutical composition is a pharmaceutical composition used as an antimicrobial agent.

[19] A method for producing a liquid formulation comprising a hydroxamic acid derivative or a salt thereof and a solubilizing agent, the method comprising: a step of dissolving the hydroxamic acid derivative selected from Compound A, Compound B and Compound C or a salt thereof and the solubilizing agent in water to obtain an aqueous solution of the hydroxamic acid derivative or the salt thereof, followed by adjusting a pH of the obtained aqueous solution to from 3 to 8, as required.

[20] The production method according to [19], wherein the solubilizing agent is CD or a CD derivative.

[21] The production method according to [19] or [20], wherein the hydroxamic acid derivative is Compound A.

[22] The production method according to [20] or [21], wherein the CD or the CD derivative is one or more selected from αCD, γCD, HPαCD, SBEβCD, 2,3,6-tri-O-methyl-β-cyclodextrin, hydroxyethyl-β-cyclodextrin, HPβCD, DMβCD, 6-O-α-maltosyl-β-cyclodextrin, methyl-β-cyclodextrin and HPγCD.

[23] The production method according to [20] or [21], wherein the CD or the CD derivative is one or more selected from αCD, γCD, HPαCD, SBEβCD, HPβCD and HPγCD.

The present invention also provides the following.

[24] The pharmaceutical composition according to any one of [1] to [11], further comprising a pH adjuster.

[25] The pharmaceutical composition according to [24], wherein the pH adjuster is one or more selected from mineral acids, organic acids, inorganic bases and organic bases.

[26] The pharmaceutical composition according to [25], wherein the mineral acid is hydrochloric acid, sulfuric acid, phosphoric acid and nitric acid; the organic acid is maleic acid, benzoic acid, ascorbic acid, methanesulfonic acid, acetic acid, malic acid, lactic acid, tartaric acid, citric acid, gluconic acid, glutamic acid, aspartic acid and adipic acid; the inorganic base is sodium hydroxide, potassium hydroxide, sodium carbonate, sodium hydrogen carbonate, sodium dihydrogen phosphate, potassium dihydrogen phosphate, disodium hydrogen phosphate, dipotassium hydrogen phosphate, trisodium phosphate and ammonia; and the organic base is disodium citrate, monoethanolamine, diethanolamine, trometamol, diisopropanolamine, triethanolamine, triisopropanolamine, L-arginine, L-histidine, L-lysine and meglumine.

[27] The pharmaceutical composition according to [25], wherein the mineral acid is hydrochloric acid and sulfuric acid; the organic acid is acetic acid and citric acid; the inorganic base is sodium hydroxide and sodium carbonate; and the organic base is trometamol and meglumine.

[28] The pharmaceutical composition according to any one of [24] to [27], wherein the pharmaceutical composition is a liquid formulation.

[29] The pharmaceutical composition according to [28], wherein a pH of the liquid formulation is from 3 to 8.

[30] The pharmaceutical composition according to any one of [24] to [27], wherein the pharmaceutical composition is a frozen liquid formulation.

[31] The pharmaceutical composition according to [30], wherein a pH of the frozen liquid formulation when thawed is from 3 to 8.

[32] The pharmaceutical composition according to any one of [24] to [27], wherein the pharmaceutical composition is a lyophilized formulation.

[33] The pharmaceutical composition according to [32], wherein a pH of an injection formulation prepared from the lyophilized formulation is from 3 to 8.

[34] The pharmaceutical composition according to any one of [24] to [33], wherein the pharmaceutical composition is a pharmaceutical composition used as an LpxC inhibitor.

[35] The pharmaceutical composition according to any one of [24] to [33], wherein the pharmaceutical composition is a pharmaceutical composition used as an antimicrobial agent.

[36] The pharmaceutical composition according to any one of [1] to [16] and [24] to [33], wherein the pharmaceutical composition is a pharmaceutical composition used for treatment of Gram-negative bacterial infection.

Advantageous Effects of the Invention

The pharmaceutical composition comprising the hydroxamic acid derivative of the present invention or a salt thereof and a solubilizing agent exhibits potent antimicrobial activity, has excellent water solubility, and is useful as a medicine. Furthermore, the production method according to the present invention is useful as a method for producing a liquid formulation comprising a pharmaceutical composition having excellent stability.

MODE FOR CARRYING OUT THE INVENTION

The present invention will be described in detail below.
"%" means herein "% by mass," unless otherwise indicated.
Treatment means prophylaxis, therapy or the like against diseases.
<Hydroxamic Acid Derivative>
Examples of the hydroxamic acid derivative include hydroxamic acid derivatives selected from Compound A, Compound B and Compound C, and Compound A is preferred.
The hydroxamic acid derivative can be produced in accordance with, for example, Production Examples described below.
When the hydroxamic acid derivative or a salt thereof has isomers (for example, optical isomers, geometrical isomers and tautomers), the present invention encompasses these isomers and also encompasses their solvates, hydrates, and crystals of various forms.
Examples of the salt of the hydroxamic acid derivative include salts with alkali metal, such as sodium and potassium; salts with alkaline earth metal, such as calcium and magnesium; ammonium salts; and salts with nitrogen-containing organic bases, such as trimethylamine, triethylamine, tributylamine, pyridine, N,N-dimethylaniline, N-methylpiperidine, N-methylmorpholine, diethylamine, dicyclohexylamine, dibenzylamine, N-benzyl-β-phenethylamine, 1-ephenamine and N,N'-dibenzylethylenediamine.
Preferred salts among the salts described above include pharmacologically acceptable salts.
Administration methods, doses and frequency of administration of the hydroxamic acid derivative or a salt thereof may be selected as appropriate depending on the age, body weight and condition of a patient. Usually for adults, it may be orally or parenterally (for example, by injection, infusion, or administration to the rectal site) administered in an amount of 0.01 to 1000 mg/kg/day in one to several portions.
<Solubilizing Agent>
In the present invention, a solubilizing agent can be used to achieve excellent solubility of the hydroxamic acid derivative or a salt thereof.
Examples of the solubilizing agents include monoalcohols, polyhydric alcohols, amides, sulfoxides, amino acids, surfactants, acids, bases, CDs and CD derivatives.
Examples of the monoalcohols include alcohols having 1 to 6 carbon atoms, such as ethanol, propanol, 2-propanol, butanol and chlorobutanol; alcohols having 7 to 20 carbon atoms, such as 3-indolepropanol, benzyl alcohol, octanol, nonanol, decanol, undecyl alcohol, lauryl alcohol, tridecyl alcohol, myristyl alcohol, pentadecyl alcohol, cetyl alcohol, heptadecyl alcohol and stearyl alcohol; and unsaturated alcohols having 7 to 20 carbon atoms, such as oleyl alcohol, linoleyl alcohol and linolenyl alcohol.

Preferred monoalcohols include alcohols having 1 to 6 carbon atoms and alcohols having 7 to 20 carbon atoms. Alcohols having 1 to 6 carbon atoms and benzyl alcohol are preferred, ethanol, propanol, 2-propanol, butanol and benzyl alcohol are more preferred, ethanol and benzyl alcohol are further preferred, and ethanol is particularly preferred.

Examples of the polyhydric alcohols include diols, such as ethylene glycol, propylene glycol, 1,3-propanediol, 1,2-butanediol, 1,3-butanediol, 1,4-butanediol, 2,3-butanediol, 1,5-pentanediol, dipropylene glycol, diethylene glycol, triethylene glycol, polyethylene glycol 300, polyethylene glycol 400, polyethylene glycol 600, polyethylene glycol 1500, polyethylene glycol 4000 and alpha-thioglycerin; and triols, such as glycerin.

Preferred polyhydric alcohols include diols. Propylene glycol, 1,3-butanediol, dipropylene glycol, diethylene glycol, triethylene glycol, polyethylene glycol 300, polyethylene glycol 400, polyethylene glycol 600, polyethylene glycol 1500 and polyethylene glycol 4000 are more preferred, and triethylene glycol and polyethylene glycol 400 are further preferred.

Examples of the amides include N,N-dimethylacetamide, polyvinyl pyrrolidone, urea, ethyl urea and nicotinic acid amide.

Preferred amides include N,N-dimethylacetamide, urea, ethyl urea and nicotinic acid amide. N,N-dimethylacetamide and nicotinic acid amide are more preferred.

Examples of the sulfoxides include dimethyl sulfoxide.

Examples of the amino acids include amino acids, such as glycine, alanine, β-alanine, valine, leucine, isoleucine, serine, threonine, cysteine, methionine, aspartic acid, glutamic acid, asparagine, glutamine, arginine, lysine, histidine, hydroxylysine, phenylalanine, tyrosine, tryptophan, N-acetyltryptophan, proline, hydroxyproline, cystine, L-glutamic acid L-lysine, taurine, β-alanine tert-butyl ester and phenylalanine tert-butyl ester, derivatives thereof, and salts thereof.

Preferred amino acids include glycine, alanine, β-alanine, aspartic acid, glutamic acid, arginine, lysine, histidine, hydroxylysine, phenylalanine, tryptophan, N-acetyltryptophan, proline, hydroxyproline, taurine, β-alanine tert-butyl ester and phenylalanine tert-butyl ester. β-Alanine, arginine, histidine, phenylalanine, tryptophan, N-acetyltryptophan, proline, taurine, β-alanine tert-butyl ester and phenylalanine tert-butyl ester are more preferred, and β-alanine, phenylalanine and tryptophan are further preferred.

Examples of the surfactants include sodium lauryl sulfate, dioctyl sodium sulfosuccinate, polysorbates, polyoxyethylene hydrogenated castor oil, Cremophor and sucrose fatty acid esters.

Preferred surfactants include polysorbates, polyoxyethylene hydrogenated castor oil, Cremophor and sucrose fatty acid esters.

Examples of the acids include organic acids, such as maleic acid, benzoic acid, ascorbic acid, methanesulfonic acid, acetic acid, malic acid, lactic acid, tartaric acid, citric acid, gluconic acid, adipic acid, succinic acid, thioglycolic acid, deoxycholic acid, ursodeoxycholic acid, edetic acid, salicylic acid, meta-sulfobenzoic acid, cinnamic acid, 3-phenylpropionic acid, 3-(4-hydroxyphenyl)propionic acid, besylic acid, p-toluenesulfonic acid, sugar acid and chondroitin sulfate; saturated fatty acids having 8 to 20 carbon atoms, such as caprylic acid, pelargonic acid, capric acid, undecylic acid, lauric acid, tridecylic acid, myristic acid, pentadecylic acid, palmitic acid, margaric acid and stearic acid; unsaturated fatty acids having 8 to 20 carbon atoms, such as citronellic acid, undecylenic acid, linderic acid, physeteric acid, zoomaric acid, palmitoleic acid, oleic acid and linoleic acid; and inorganic acids, such as hydrochloric acid, sulfuric acid, phosphoric acid, nitric acid, sodium dihydrogen phosphate and potassium dihydrogen phosphate.

Preferred acids include organic acids. Maleic acid, benzoic acid, ascorbic acid, methanesulfonic acid, acetic acid, lactic acid, tartaric acid, citric acid, gluconic acid, adipic acid, thioglycolic acid, deoxycholic acid, ursodeoxycholic acid, salicylic acid, meta-sulfobenzoic acid, cinnamic acid, 3-phenylpropionic acid, 3-(4-hydroxyphenyl)propionic acid, besylic acid and p-toluenesulfonic acid are more preferred, benzoic acid, citric acid, cinnamic acid, 3-phenylpropionic acid, 3-(4-hydroxyphenyl)propionic acid and p-toluenesulfonic acid are further preferred, and benzoic acid is particularly preferred.

Examples of the bases include salts of organic acids, such as disodium citrate, sodium citrate, sodium acetate, sodium lactate, magnesium gluconate, calcium saccharate and sodium benzoate; organic bases, such as monoethanolamine, diethanolamine, trometamol, diisopropanolamine, triethanolamine, triisopropanolamine, ethylenediamine and meglumine; and inorganic bases, such as sodium hydroxide, potassium hydroxide, sodium carbonate, potassium carbonate, sodium hydrogen carbonate, disodium hydrogen phosphate, dipotassium hydrogen phosphate, trisodium phosphate and ammonia.

Preferred bases include disodium citrate, sodium citrate, sodium acetate, sodium lactate, magnesium gluconate, calcium saccharate, sodium benzoate, diethanolamine, trometamol, diisopropanolamine, triethanolamine, ethylenediamine, meglumine, sodium hydroxide, sodium carbonate, sodium hydrogen carbonate, disodium hydrogen phosphate and trisodium phosphate. Sodium citrate, sodium lactate, sodium benzoate, trometamol, meglumine and sodium hydroxide are more preferred.

Examples of the CDs include αCD, β-cyclodextrin (sometimes referred to as "βCD" hereinbelow), or γCD.

Examples of the CD derivative include HPαCD, dimethyl-β-cyclodextrin, SBEβCD, 2,3,6-triacetyl-β-cyclodextrin, 2,3,6-tri-O-methyl-β-cyclodextrin, hydroxyethyl-β-cyclodextrin, HPβCD, DMβCD, 6-O-α-maltosyl-β-cyclodextrin, methyl-β-cyclodextrin, monoacetyl-β-cyclodextrin, monochlorotriazino-β-cyclodextrin, or HPγCD.

Preferred CDs or CD derivatives include αCD, γCD, HPαCD, SBEβCD, 2,3,6-tri-O-methyl-β-cyclodextrin, hydroxyethyl-β-cyclodextrin, HPβCD, DMβCD, 6-O-α-maltosyl-β-cyclodextrin, methyl-β-cyclodextrin, or HPγCD. αCD, γCD, HPαCD, SBEβCD, HPβCD, or HPγCD is more preferred.

Preferred solubilizing agents of the present invention include CDs and CD derivatives.

Additionally, preferred solubilizing agents of the present invention include one or more selected from monoalcohols, polyhydric alcohols, amides, sulfoxides, amino acids, surfactants, acids and bases. A combination of one or more selected from alcohols having 1 to 6 carbon atoms, diols, amino acids and organic acids with an amide is more preferred.

The pharmaceutical composition of the present invention is provided as a liquid formulation, a frozen liquid formulation, or a lyophilized formulation.

Subsequently, the method for producing the pharmaceutical composition of the present invention will be described.

Production Method 1 Liquid Formulation

The liquid formulation can be produced by dissolving a hydroxamic acid derivative or a salt thereof and a solubilizing agent in water.

The hydroxamic acid derivative is preferably Compound A.

The solubilizing agent is preferably a CD or a CD derivative.

The amount of the solubilizing agent should be sufficient to dissolve the hydroxamic acid derivative or the salt thereof. The amount may be usually 1 to 20 molar times, and is preferably 1.2 to 10 molar times, and more preferably 1.5 to 5 molar times, relative to the hydroxamic acid derivative or the salt thereof.

In another aspect, the preferred solubilizing agent is one or more selected from monoalcohols, polyhydric alcohols, amides, sulfoxides, amino acids, surfactants, acids and bases.

It should be noted that sterilization treatment and the like in the production of the liquid formulation of the present invention may be conducted in accordance with the procedures usually performed.

The pH of a liquid formulation of the present invention is preferably from 3 to 8, more preferably from 3.5 to 7.5, and further preferably from 4.0 to 6.5.

The pH of the liquid formulation is preferably adjusted to from 3 to 8, more preferably to from 3.5 to 7.5, and further preferably to from 4.0 to 6.5 by adding a pH adjuster as required.

Examples of the pH adjuster used include one or more selected from mineral acids, organic acids, inorganic bases and organic bases.

Examples of the mineral acid used as the pH adjuster include hydrochloric acid, sulfuric acid, phosphoric acid and nitric acid. Hydrochloric acid, sulfuric acid and phosphoric acid are preferred, and hydrochloric acid and sulfuric acid are more preferred.

Examples of the organic acid used as the pH adjuster include maleic acid, benzoic acid, ascorbic acid, methanesulfonic acid, acetic acid, malic acid, lactic acid, tartaric acid, citric acid, gluconic acid, glutamic acid, aspartic acid and adipic acid. Ascorbic acid, methanesulfonic acid, acetic acid, citric acid and aspartic acid are preferred, and acetic acid and citric acid are more preferred.

Examples of the inorganic base used as the pH adjuster include sodium hydroxide, potassium hydroxide, sodium carbonate, sodium hydrogen carbonate, sodium dihydrogen phosphate, potassium dihydrogen phosphate, disodium hydrogen phosphate, dipotassium hydrogen phosphate, trisodium phosphate and ammonia. Sodium hydroxide, sodium carbonate, sodium hydrogen carbonate and trisodium phosphate are preferred, and sodium hydroxide and sodium carbonate are more preferred.

Examples of the organic base used as the pH adjuster include disodium citrate, monoethanolamine, diethanolamine, trometamol, diisopropanolamine, triethanolamine, triisopropanolamine, L-arginine, L-histidine, L-lysine and meglumine. Monoethanolamine, diethanolamine, trometamol, triethanolamine and meglumine are preferred, and trometamol and meglumine are more preferred.

Additives usually used, such as osmo-regulators, stabilizers, surfactants, soothing agents, excipients and/or preservatives, may be added to the liquid formulation of the present invention, as required.

Examples of the osmo-regulator include glucose, sodium chloride, D-mannitol, glycerin and propylene glycol.

Examples of the stabilizer include sodium hydrogen sulfite, sodium metabisulfite, potassium metabisulfite, sodium pyrophosphate, sodium thiosulfate, sodium metasulfobenzoate, sodium formaldehydesulfoxylate, ethylenediamine, disodium edetate, thioglycolic acid, sodium gluconate, potassium L-glutamate, L-lysine-L-glutamate, chondroitin sulfate sodium, L-aspartic acid, L-cysteine and dibutylhydroxytoluene.

Examples of the surfactant include sorbitan fatty acid esters, polyoxyethylene hydrogenated castor oil, polyoxyethylene sorbitan fatty acid esters and polyoxyethylene-polyoxypropylene glycol copolymers.

Examples of the soothing agent include lidocaine, procaine, meprylcaine and benzyl alcohol.

Examples of the excipient include sugars such as trehalose, maltose, glucose, lactose, sucrose and fructose, sugar alcohols such as D-sorbitol, xylitol, inositol and D-mannitol, or amino acids such as glycine, L-alanine, L-phenylalanine, L-leucine, L-isoleucine, taurine, DL-methionine, L-serine, L-threonine, L-glutamine, sodium L-glutamate, acetyltryptophan and L-histidine.

Examples of the preservative include methyl parahydroxybenzoate, ethyl parahydroxybenzoate, propyl parahydroxybenzoate, butyl parahydroxybenzoate, disodium edetate, tetrasodium edetate, chlorobutanol, chlorhexidine gluconate, benzalkonium chloride and benzethonium chloride.

The liquid formulation of the present invention can be provided as an injection liquid formulation.

The content of the hydroxamic acid derivative in the liquid formulation of the present invention is preferably from 1 to 100 mg/mL, more preferably from 2 to 50 mg/mL.

The dose of the hydroxamic acid derivative is determined as appropriate, depending on usages, the age and sex of the patient, disease forms, other conditions, and the like. Usually, the derivative may be administered in an amount of 0.1 to 1000 mg/kg/day to an adult.

Production Method 2 Frozen Liquid Formulation

The frozen liquid formulation can be produced by freezing the liquid formulation obtained by the method described in Production method 1.

The temperature of the freezing step should be temperatures at which the liquid formulation can be frozen, and the temperature is preferably from −78 to −15° C.

The time period of the freezing step may be, but not particularly limited to, from 1 to 24 hours.

It should be noted that sterilization treatment and the like in the production of the frozen liquid formulation of the present invention may be conducted in accordance with the procedures usually performed.

The frozen liquid formulation of the present invention can be thawed to be provided as an injection liquid formulation.

The pH of the frozen liquid formulation when thawed is preferably from 3 to 8, more preferably from 3.5 to 7.5, and further preferably from 4.0 to 6.5.

The content of the hydroxamic acid derivative in the frozen liquid formulation when thawed is preferably from 1 to 100 mg/mL, more preferably from 2 to 50 mg/mL.

The dose of the hydroxamic acid derivative is determined as appropriate, depending on usages, the age and sex of the patient, disease forms, other conditions, and the like. Usually, the derivative may be administered in an amount of 0.1 to 1000 mg/kg/day to an adult.

Production Method 3 Lyophilized Formulation

The lyophilized formulation can be provided by lyophilizing the liquid formulation obtained by the method described in Production method 1.

This step may be conducted in accordance with a lyophilized method usually conducted. For example, the step can be conducted in accordance with "15.2 Touketsu kansou no jissai (Practical lyophilization)" described in "Iyakuhin no jissai (Practical pharmaceuticals)," Vol. 11, Seizai no tanisousa to kikai (Unit operation and machines for pharmaceutical), edited by Yoshinobu Nakai, pp. 388 to 396 (1988, Hirokawa Shoten Co.).

To the lyophilized formulation of the present invention, additives can be added to improve the solubility and/or appearance.

Examples of the additive include amino acids, polyethylene glycols, sugars, sugar alcohols, urea, ethyl urea, creatinine, trometamol, purified soya lecitin and polysorbate 80. These can be used singly or in mixture of two or more.

Preferred additives include amino acids, polyethylene glycols, sugars and sugar alcohols. Amino acids, sugars and sugar alcohols are more preferred, and sugar alcohols are further preferred.

Examples of the amino acid used as an additive include glycine, L-alanine, L-phenylalanine, L-valine, L-leucine, L-isoleucine, taurine, DL-methionine, L-serine, L-threonine, L-glutamine, sodium L-glutamate, acetyltryptophan and L-histidine. Glycine, L-serine, L-threonine, L-alanine, L-leucine and L-isoleucine are preferred, and glycine is more preferred.

Examples of the polyethylene glycol used as an additive include polyethylene glycol 300, polyethylene glycol 400, polyethylene glycol 600, polyethylene glycol 4000 and polyethylene glycol 6000. Polyethylene glycol 300, polyethylene glycol 600 and polyethylene glycol 4000 are preferred.

Examples of the sugar used as an additive include trehalose, maltose, glucose, lactose, sucrose, fructose and dextran. Trehalose, glucose, sucrose and fructose are preferred.

Examples of the sugar alcohol used as an additive include D-sorbitol, xylitol, inositol and D-mannitol. D-sorbitol, xylitol and D-mannitol are preferred.

In the production of the lyophilized formulation of the present invention, the sterilization treatment and the like may be conducted in accordance with the procedures usually performed.

The lyophilized formulation of the present invention can be dissolved with water for injection and the like to be provided as an injection formulation.

The pH of the injection formulation prepared from the lyophilized formulation is preferably from 3 to 8, more preferably from 3.5 to 7.5, and further preferably from 4.0 to 6.5.

The content of the hydroxamic acid derivative in the injection formulation prepared from the lyophilized formulation is preferably from 1 to 100 mg/mL, more preferably from 2 to 50 mg/mL.

The dose of the hydroxamic acid derivative is determined as appropriate, depending on usages, the age and sex of the patient, disease forms, other conditions, and the like. Usually, the derivative may be administered in an amount of 0.1 to 1000 mg/kg/day to an adult.

The liquid formulation, frozen liquid formulation and lyophilized formulation of the present invention are preferably produced without using organic solvent. Thus, these formulations contain no residual solvent and are safe for human bodies.

The present invention will be described referring to Production Examples, Examples and Test Examples, but the present invention is not intended to be limited to these.

Unless specifically mentioned, the silica gel column chromatography is flash column chromatography, and its carrier is B.W. silica gel BW-300, Fuji Silysia Chemical Ltd.

The mixture ratio in the eluant is the volume ratio.

The conditions of lyophilization are as follows.

A vial is cooled to −60° C. to freeze its content. Then, the shelf temperature is increased to −10° C. in vacuo (50 Pa or less), and primary drying is carried out at the same pressure and temperature. When the product temperature has reached −10° C. or more, the shelf temperature is increased to 20° C., and secondary drying is carried out at the same pressure and temperature. The drying is considered to be completed when the product temperature approximately corresponds to the setting temperature and exhibits no change.

Each abbreviation has the following meaning.
DMSO-$d_6$: Heavy dimethyl sulfoxide
ESI: Electrospray ionization
IPE: Diisopropyl ether
Me: Methyl
TBS: tert-Butyldimethylsilyl
THP: Tetrahydro-2H-pyran-2-yl
s: Singlet
d: Doublet
dd: Double doublet
m: Multiplet In a $^1$H-NMR spectrum, for example, the description of [1.81], 1.82 (3H, s) indicates that peaks derived from each diastereomer in a diastereomer mixture are observed at 1.81 and 1.82 as a singlet, and the total number of protons is 3H.

Production Example 1

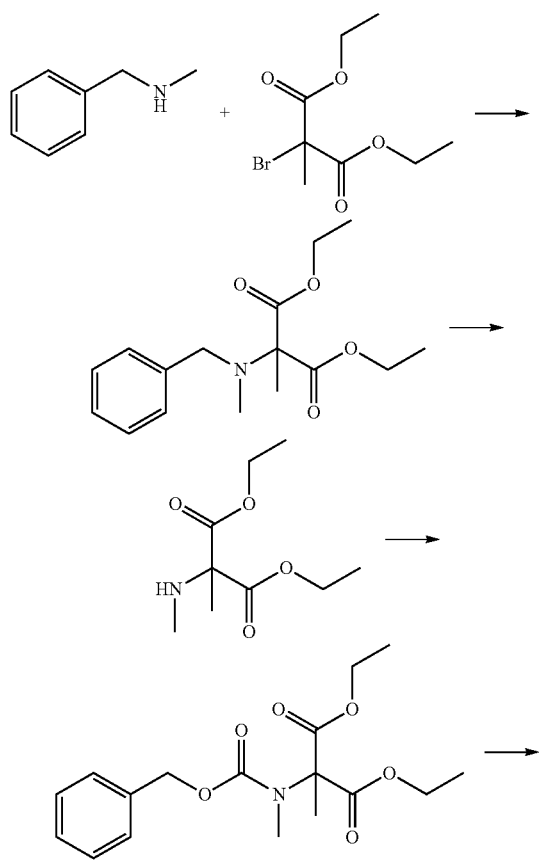

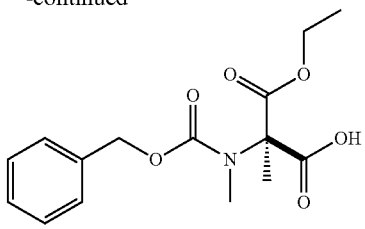

To 1000 mL of N-methylpyrrolidone, 421 g of N-methylbenzylamine and 400 g of diethyl 2-bromo-2-methylmalonate were added and stirred at 100° C. for an hour. Then, the reaction mixture was cooled. After 1.5 L of toluene and 1.5 L of water were added sequentially, 70 mL of hydrochloric acid was added. The organic layer was separated, and the solvent was distilled off under reduced pressure to obtain 499 g of a colorless oily product.

To 400 g of the obtained oily product, 2.0 L of ethyl acetate, 32 g of 10% palladium on carbon (50% wet) and 81.9 g of acetic acid were added sequentially and stirred under hydrogen atmosphere (0.5 MPa) at 45° C. for 18 hours and 30 minutes. After the reaction mixture was cooled and filtered over celite, the residue was washed with 400 mL of ethyl acetate. To the filtrate, 1200 mL of water was added. Hydrochloric acid was used to adjust the pH to 2 or less, and the aqueous layer was separated. To the obtained aqueous layer, 1200 mL of ethyl acetate was added, and a 20% sodium hydroxide aqueous solution was used to adjust the pH to 9. The organic layer was separated and the solvent was distilled off under reduced pressure to obtain 204 g of a colorless oily product.

To 200 g of the obtained oily product, 1.0 L of acetonitrile and 198 g of sodium hydrogen carbonate were added. Then, 168 g of benzyl chloroformate was added dropwise under ice cooling over 25 minutes. The reaction mixture was warmed to room temperature, stirred for 7 hours and 45 minutes, and allowed to stand overnight. Then, the reaction mixture was stirred at 40 to 45° C. for 1 hour and 30 minutes, and cooled, and then, an insoluble material was filtered off. The residue was washed with 200 mL of acetonitrile. The filtrate and the washed solution were combined and concentrated under reduced pressure to obtain 324 g of a colorless oily product.

To 1968 mL of water, 15.36 g of sodium dihydrogen phosphate dihydrate was added, and 1125 mL of a 0.05 mol/L sodium hydroxide aqueous solution was added. To this aqueous solution, a mixture of 120 g of the obtained oily product and 360 mL of acetonitrile was added at 24° C., stirred at the same temperature for 2 hours and 45 minutes, and then, allowed to stand overnight. Additionally, the reaction mixture was stirred at the same temperature for 6 hours, and then, allowed to stand for 22 hours. Subsequently, 30 mL of a 0.05 mol/L phosphate buffer solution (pH 7.4) was added to 2.9 g (20 units/mg) of porcine liver esterase and subjected to ultrasonic irradiation for 30 minutes to provide a suspension solution, which was added to the reaction mixture at 25° C. The reaction mixture, of which pH was adjusted with a 1 mol/L sodium hydroxide aqueous solution within the range of 6.7 to 7.1, was stirred at 26° C. for 5 hours. To the reaction mixture, 1200 mL of ethyl acetate was added, and 37 mL of hydrochloric acid, 300 g of sodium chloride and 48 g of Celpure were added sequentially under ice cooling. After stirring at the same temperature for an hour, an insoluble material was filtered off. The residue was washed with 240 mL of ethyl acetate, and the filtrate and the washed solution were combined. The organic layer was separated, and the aqueous layer was extracted with 180 mL of ethyl acetate. The organic layer and the extract solution were combined, and 48 g of anhydrous sodium sulfate and 1.2 g of activated carbon were added. After stirring for 30 minutes, the mixture was filtered over celite. The residue was washed with 180 mL of ethyl acetate, and the filtrate and the washed solution were combined. Then, 1540 mL of the solvent was distilled off under reduced pressure. To the obtained residue, 240 mL of heptane was added and cooled to 18° C. over 2 hours. The solid was filtered off and washed with 120 mL of heptane twice to obtain 88.18 g (>99.9% ee) of (((((2R)-2-carboxy-1-ethoxy-1-oxopropan-2-yl)(methyl)carbamoyl)oxy)methyl)benzene as colorless crystals.

$^1$H-NMR (400 MHz, DMSO-d$_6$) δ: 1.15-1.20 (3H, m), 1.61 (3H, s), 2.86 (3H, s), 3.95-4.15 (2H, m), 5.07 (2H, s), 7.28-7.43 (5H, m)

HPLC Measurement Conditions
  Column: 4.6×150 mm CHIRALPAK IA 5 m
  Measurement wavelength: 210 nm
  Column temperature: 40° C.
  Mobile phase: hexane:ethanol=95:5 (0.1% trifluoroacetic acid)
  Flow rate: 0.7 mL/minute Production Example 2

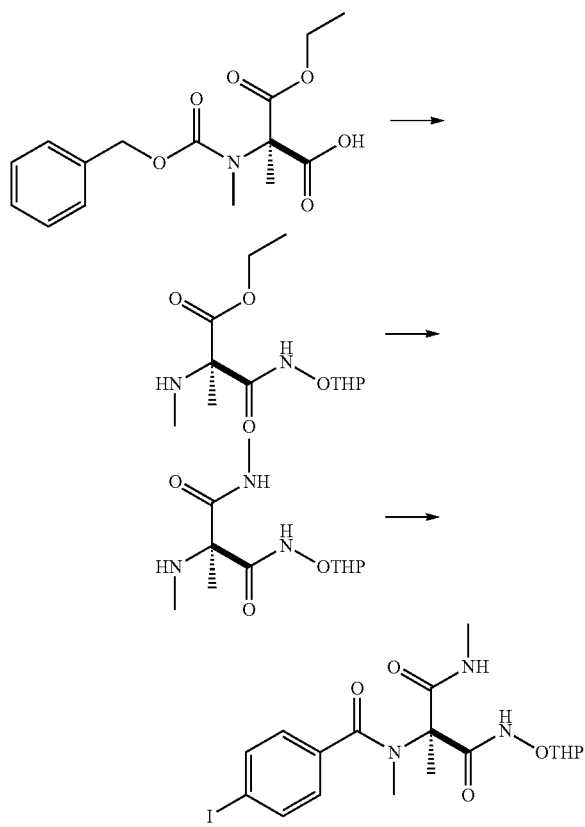

To 250 g of (((((2R)-2-carboxy-1-ethoxy-1-oxopropan-2-yl)(methyl)carbamoyl)oxy)methyl)benzene, 1300 mL of ethyl acetate and 1.0 mL of N,N-dimethylformamide were added. After 133 g of oxalyl chloride was added dropwise at 5° C. over 20 minutes, 200 mL of ethyl acetate was added. The reaction mixture was warmed to 20° C. and stirred for 4 hours. Under reduced pressure, 1395 mL of the solvent was distilled off. To the obtained residue, 1000 mL of tetrahydrofuran was added and cooled to 8° C. At the same temperature, 94.1 g of triethylamine and 109 g of O-(tetrahydro-2H-pyran-2-yl)hydroxylamine were added sequentially, and warmed to 20° C. over 3 hours with stirring. After the reaction mixture was allowed to stand overnight, 225 mL of acetone was added and stirred for 40 minutes. Subsequently, 750 mL of toluene and 1000 mL water were added and cooled to 10° C. Then 62 mL of hydrochloric acid was added. Additionally, the pH was adjusted to 3 with 6 mol/L hydrochloric acid and a 20% sodium hydroxide aqueous solution, and the aqueous layer was separated. To the obtained aqueous layer, 1250 mL of ethyl acetate was added, and 210 mL of a 20% sodium hydroxide aqueous solution was added. Subsequently, 1450 g of sodium chloride was added, and the resultant solution was warmed to 30° C. The organic layer was separated, and the aqueous layer was extracted with 750 mL of ethyl acetate. The organic layer and the extract solution were combined, and the solvent was distilled off under reduced pressure. To the obtained residue, 250 mL of toluene was added. The solvent was distilled off under reduced pressure to obtain 215 g of an orange oily product.

To 213 g of the obtained oily product, a 40% methylamine/methanol solution was added at room temperature, stirred at 40 to 43° C. for 8 hours and 30 minutes, and then, allowed to stand overnight. Additionally, after stirring at 45° C. for 5 hours, the solvent was distilled off under reduced pressure. To the obtained residue, toluene was added, and the solvent was distilled off under reduced pressure. Subsequently, tetrahydrofuran was added to the obtained residue, and the solvent was distilled off under reduced pressure to obtain 203 g of a yellow oily product.

To 203 g of the obtained oily product, 1400 mL of tetrahydrofuran was added, and 117 g of sodium hydrogen carbonate was added at 35° C. Subsequently, a mixture of 168 g of 4-iodobenzoyl chloride and 200 mL of tetrahydrofuran, and 100 mL of tetrahydrofuran were added at the same temperature and stirred for 5 hours. After 58.2 g of sodium hydrogen carbonate and 29 mL of morpholine were added to the reaction mixture at the same temperature and stirred for 2 hours, the mixture was allowed to stand overnight at room temperature. To the reaction mixture, 1370 mL of ethyl acetate, 1700 mL of water and 170 g of sodium chloride were added sequentially, and the organic layer was separated. After 860 mL of water and 42.7 g of sodium chloride were added to the obtained organic layer and stirred for 15 minutes, the organic layer was separated. The obtained organic layer was filtered, and the solvent of the filtrate was distilled off under reduced pressure. After 300 mL of ethyl acetate and 300 mL of toluene were added to the obtained residue and stirred at 30° C. for an hour, the mixture was allowed to stand overnight. The solid was filtered off and washed with an ethyl acetate/toluene mixture (1:1, 300 mL) to obtain 206 g of a brown solid. After 2000 mL of ethyl acetate was added to the obtained brown solid and stirred at 40° C. for an hour, the mixture was cooled under ice cooling, and the solid was filtered off. The solid was washed with ethyl acetate to obtain 148.9 g (>99.9% ee) of (2S)-2-((4-iodobenzoyl)(methyl)amino)-N,2-dimethyl-N'-(tetrahydro-2H-pyran-2-yloxy)malonamide as colorless crystals.

$^1$H-NMR (400 MHz, DMSO-d$_6$) δ: 1.40-1.75 (6H, m), 1.61 (3H, s), [2.62] 2.63 (3H, d, J=3.7 Hz), 2.99 (3H, d, J=2.7 Hz), 3.40-3.60 (1H, m), [3.82-3.92] 3.92-4.02 (1H, m), [4.74-4.80] 4.80-4.86 (1H, m), [7.31] 7.33 (2H, d, J=8.2 Hz), 7.85 (2H, d, J=8.3 Hz), [8.25-8.33] 8.35-8.43 (1H, m), 11.52 (1H, s)

HPLC Measurement Conditions
  Column: 4.6×250 mm CHIRALPAK ID 5 μm
  Measurement wavelength: 230 nm
  Column temperature: 40° C.
  Mobile phase: hexane:ethanol=85:15
  Flow rate: 1.0 mL/minute Production Example 3

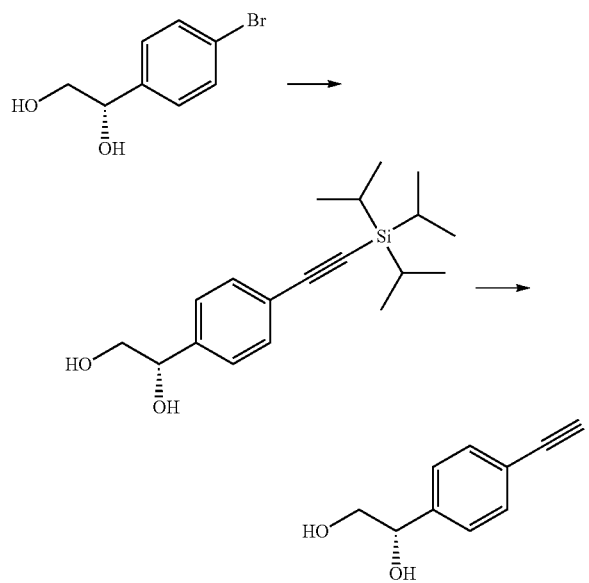

To a mixture of 1.08 g of (1S)-1-(4-bromophenyl)ethane-1,2-diol, 350 mg of bis-triphenylphosphinepalladium(II) dichloride, 190 mg of copper(I) iodide, and 10 mL of n-butyl acetate, 7.8 mL of triisopropylsilylacetylene and 7.0 mL of triethylamine were added under a nitrogen atmosphere, and the resulting mixture was stirred under reflux for 1 hour. The reaction mixture was cooled, a saturated aqueous solution of ammonium chloride was added, the pH was adjusted to 6.2 with 6 mol/L hydrochloric acid, then Celpure and ethyl acetate were added, and then the insoluble material was filtered off. The organic layer of the filtrate was separated, washed with a saturated aqueous solution of sodium chloride, and then dried over anhydrous magnesium sulfate. The solvent was distilled off under reduced pressure, and the obtained residue was subjected to silica gel column chromatography [eluent; ethyl acetate:hexane=40:60→45:55] to obtain 1.32 g of a yellow oil.

To a mixture of 1.32 g of the obtained yellow oil and 13 mL of tetrahydrofuran, 6.2 mL of a 1 mol/L solution of tetra-n-butylammonium fluoride in tetrahydrofuran was added under ice cooling, and the resulting mixture was stirred at the same temperature for 30 minutes and then at room temperature for 45 minutes. A saturated aqueous solution of ammonium chloride was added to the reaction mixture, the pH was adjusted to 2.0 with 1 mol/L hydrochloric acid, and then ethyl acetate was added. The organic layer was separated, and the aqueous layer was extracted with ethyl acetate twice. The organic layer was combined with the extract, washed with a saturated aqueous solution of sodium chloride, and then dried over anhydrous magnesium sulfate. The solvent was distilled off under reduced pressure, and the obtained residue was purified by silica gel column chromatography [eluent; ethyl acetate:hexane=50:50→70:30] to obtain 513 mg of a light brown solid. Hexane was added thereto, and the solid material was collected by filtration to obtain 466 mg of (1S)-1-(4-ethynylphenyl)ethane-1,2-diol as a light brown solid.

¹H-NMR (400 MHz, CDCl₃) δ: 1.97-2.07 (1H, m), 2.56 (1H, d, J=3.4 Hz), 3.08 (1H, s), 3.56-3.70 (1H, m), 3.71-3.82 (1H, m), 4.79-4.88 (1H, m), 7.34 (2H, d, J=8.3 Hz), 7.49 (2H, d, J=8.3 Hz)

Production Example 4

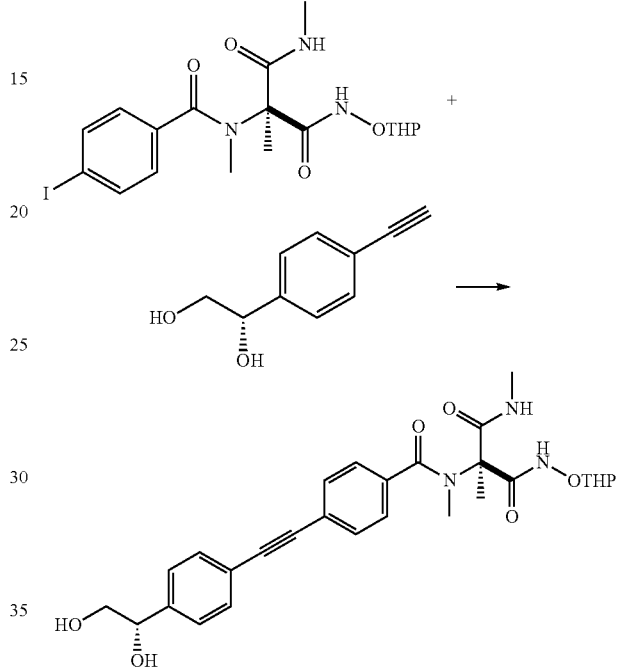

To a mixture of 587 mg of (2S)-2-((4-iodobenzoyl)(methyl)amino)-N,2-dimethyl-N'-(tetrahydro-2H-pyran-2-yloxy)malonamide, 253 mg of (1S)-1-(4-ethynylphenyl)ethane-1,2-diol, 84 mg of bis-triphenylphosphinepalladium(II) dichloride, 46 mg of copper(I) iodide, and 6.0 mL of tetrahydrofuran, 0.59 mL of triethylamine was added under a nitrogen atmosphere and under ice cooling, and the resulting mixture was stirred at the same temperature for 2 hours. A saturated aqueous solution of ammonium chloride and ethyl acetate were added to the reaction mixture, and the pH was adjusted to 6.4 with 1 mol/L hydrochloric acid. The organic layer was separated, and the aqueous layer was extracted with ethyl acetate. The organic layer was combined with the extract, washed with a saturated aqueous solution of sodium chloride, and then dried over anhydrous sodium sulfate. The solvent was distilled off under reduced pressure, and the obtained residue was purified by silica gel column chromatography [eluent; acetone:chloroform=40:60] to obtain 767 mg of (2S)-2-((4-((4-((1S)-1,2-dihydroxyethyl)phenyl)ethynyl)benzoyl)(methyl)amino)-N,2-dimethyl-N'-(tetrahydro-2H-pyran-2-yloxy)malonamide as a pale yellow foamy solid.

¹H-NMR (400 MHz, CDCl₃) δ: 1.50-1.68 (3H, m), 1.71-1.92 (3H, m), [1.82], 1.83 (3H, s), 2.08-2.14 (1H, m), 2.63-2.68 (1H, m), [2.86], 2.87 (3H, d, J=4.1 Hz), [3.17], 3.20 (3H, s), 3.53-3.83 (3H, m), 3.83-4.07 (1H, m), 4.83-4.89 (1H, m), 4.93-5.03 (1H, m), 7.37 (2H, d, J=8.0 Hz), 7.48-7.61 (6H, m), [6.97-7.04], 7.61-7.67 (1H, m), [10.10], 10.51 (1H, s)

Production Example 5

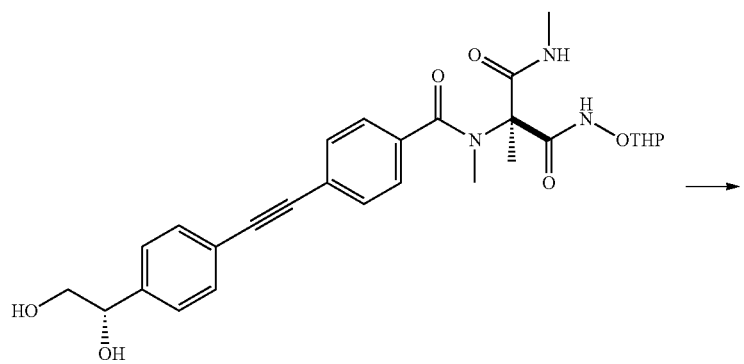

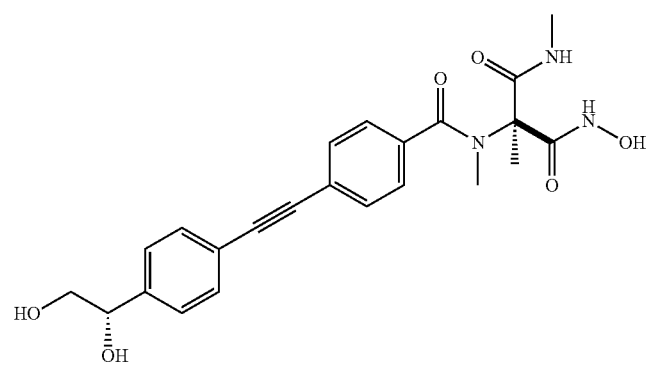

To a mixture of 767 mg of (2S)-2-((4-((4-((1S)-1,2-dihydroxyethyl)phenyl)ethynyl)benzoyl)(methyl)amino)-N,2-dimethyl-N'-(tetrahydro-2H-pyran-2-yloxy)malonamide and 6.0 mL of methanol, 46 mg of p-toluenesulfonic acid monohydrate was added under ice cooling, and the resulting mixture was stirred at the same temperature for 40 minutes and then at room temperature for 1 hour. Water and ethyl acetate were added to the reaction mixture, and the resulting mixture was neutralized with a saturated aqueous solution of sodium hydrogen carbonate. The organic layer was separated, ethyl acetate and sodium chloride were added to the aqueous layer, and the solid material was collected by filtration. The organic layer of the filtrate was separated, ethyl acetate and sodium chloride were added to the aqueous layer, and the solid material was collected by filtration. The organic layer of the filtrate was separated, the organic layer and the solid material thus obtained were combined together, and then the solvent was distilled off under reduced pressure. The obtained residue was purified by silica gel column chromatography [eluent; methanol:chloroform=10:90→15:85] to obtain 585 mg of a yellow foamy solid. Ethyl acetate and IPE were added thereto, and the solid material was collected by filtration to obtain 463 mg of (2S)-2-((4-((4-((1S)-1,2-dihydroxyethyl)phenyl)ethynyl)benzoyl)(methyl)amino)-N-hydroxy-N',2-dimethyl-malonamide (Compound A) as a yellow solid.

$^1$H-NMR (400 MHz, CD$_3$OD) δ: 1.77 (3H, s), 2.79 (3H, s), 3.17 (3H, s), 3.55-3.68 (2H, m), 4.67-4.74 (1H, m), 7.41 (2H, d, J=8.3 Hz), 7.51 (2H, d, J=8.3 Hz), 7.55 (2H, d, J=8.5 Hz), 7.68 (2H, d, J=8.5 Hz); MS (ESI): 462[M+Na]$^+$, 438[M-H]$^-$

Production Example 6

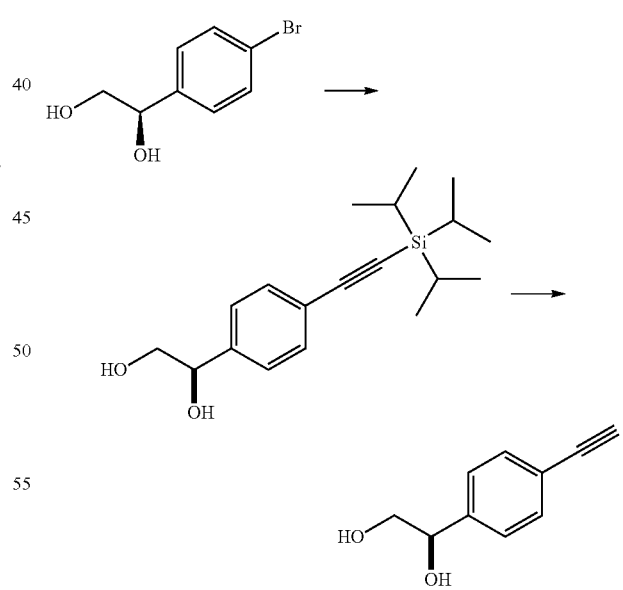

In the same manner as in Production Example 3, from 1.09 g of (1R)-1-(4-bromophenyl)ethane-1,2-diol, 558 mg of (1R)-1-(4-ethynylphenyl)ethane-1,2-diol was obtained as a white solid.

$^1$H-NMR (400 MHz, CDCl$_3$) δ: 2.00 (1H, dd, J=7.1, 4.9 Hz), 2.54 (1H, d, J=3.4 Hz), 3.08 (1H, s), 3.60-3.68 (1H, m), 3.73-3.81 (1H, m), 4.80-4.88 (1H, m), 7.34 (2H, d, J=8.1 Hz), 7.49 (2H, d, J=8.0 Hz)

Production Example 7

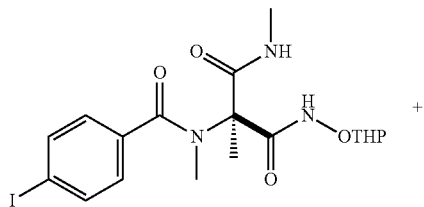

+

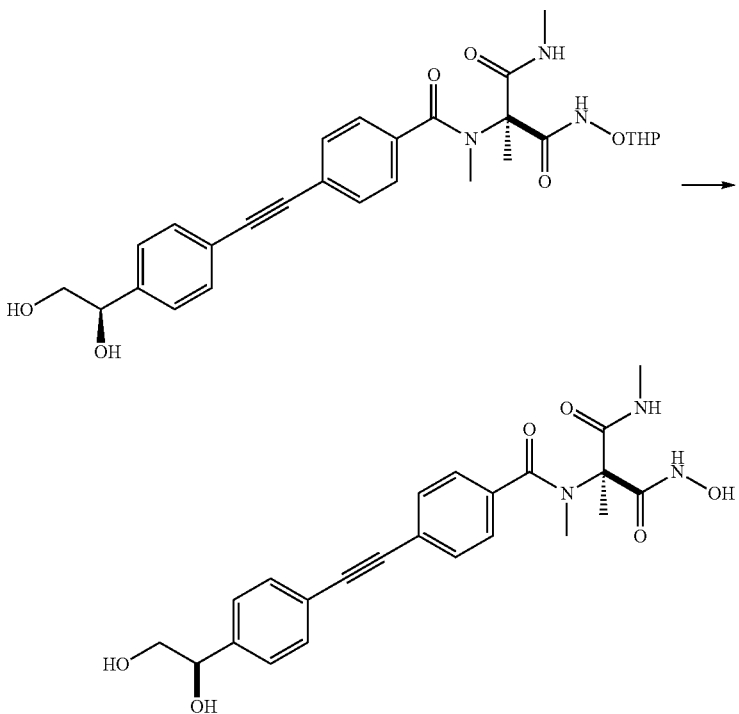

In the same manner as in Production Example 4, from 587 mg of (2S)-2-((4-iodobenzoyl)(methyl)amino)-N,2-dimethyl-N'-(tetrahydro-2H-pyran-2-yloxy)malonamide and 291 mg of (1R)-1-(4-ethynylphenyl)ethane-1,2-diol, 797 mg of (2S)-2-((4-((4-((1R)-1,2-dihydroxyethyl)phenyl)ethynyl)benzoyl)(methyl)amino)-N,2-dimethyl-N'-(tetrahydro-2H-pyran-2-yloxy)malonamide was obtained as a light brown foamy solid.

$^1$H-NMR (400 MHz, CDCl$_3$) δ: 1.53-1.69 (3H, m), 1.76-1.92 (3H, m), [1.81], 1.82 (3H, s), 2.27-2.37 (1H, m), 2.83-2.91 (4H, m), [3.17], 3.19 (3H, s), 3.53-3.83 (3H, m), [3.83-3.92], 3.98-4.08 (1H, m), 4.81-4.88 (1H, m), 4.94-5.04 (1H, m), 7.35 (2H, d, J=8.1 Hz), 7.45-7.59 (6H, m), [6.96-7.06], 7.59-7.68 (1H, m), [10.14], 10.56 (1H, s)

Production Example 8

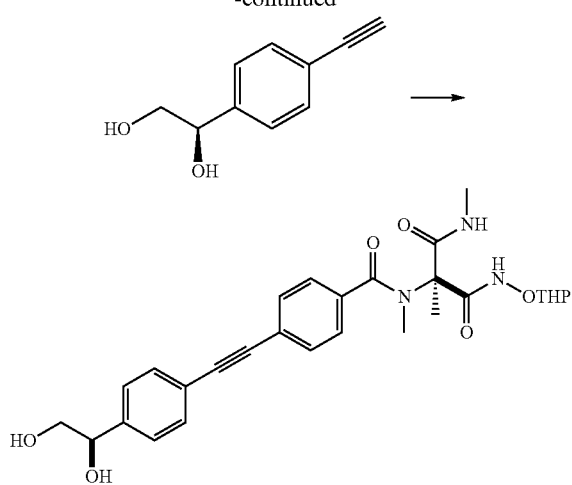

To a mixture of 797 mg of (2S)-2-((4-((4-((1R)-1,2-dihydroxyethyl)phenyl)ethynyl)benzoyl)(methyl)amino)-N,2-dimethyl-N'-(tetrahydro-2H-pyran-2-yloxy)malonamide and 6.3 mL of methanol, 46 mg of p-toluenesulfonic acid monohydrate was added under ice cooling, and the resulting mixture was stirred at the same temperature for 30 minutes and then at room temperature for 45 minutes. Water and ethyl acetate were added to the reaction mixture, and the resulting mixture was neutralized with a saturated aqueous solution of sodium hydrogen carbonate. The organic layer was separated, and the aqueous layer was extracted with ethyl acetate twice. Sodium chloride was added to the aqueous layer, and the solid material was collected by filtration. Sodium chloride and ethyl acetate were added to the filtrate, and the solid material was collected by filtration. The organic layer of the filtrate was separated, the organic layer, the extract, and the solid material thus obtained were combined together, and then the solvent was distilled off under reduced pressure. The obtained residue was purified by silica gel column chromatography [eluent; methanol:chloroform=10:90→15:85] to obtain 556 mg of a yellow foamy solid. Ethyl acetate and IPE were added thereto, and the solid material was collected by filtration to obtain 458 mg of (2S)-2-((4-((4-((1R)-1,2-dihydroxyethyl)phenyl)ethynyl)benzoyl)(methyl)amino)-N-hydroxy-N',2-dimethyl-malonamide (Compound B) as a yellow solid.

$^1$H-NMR (400 MHz, CD$_3$OD) δ: 1.78 (3H, s), 2.80 (3H, s), 3.17 (3H, s), 3.57-3.67 (2H, m), 4.68-4.74 (1H, m), 7.42 (2H, d, J=8.3 Hz), 7.52 (2H, d, J=8.3 Hz), 7.56 (2H, d, J=8.6 Hz), 7.61 (2H, d, J=8.6 Hz); MS (ESI): 462[M+Na]$^+$, 438[M-H]$^-$

Production Example 9

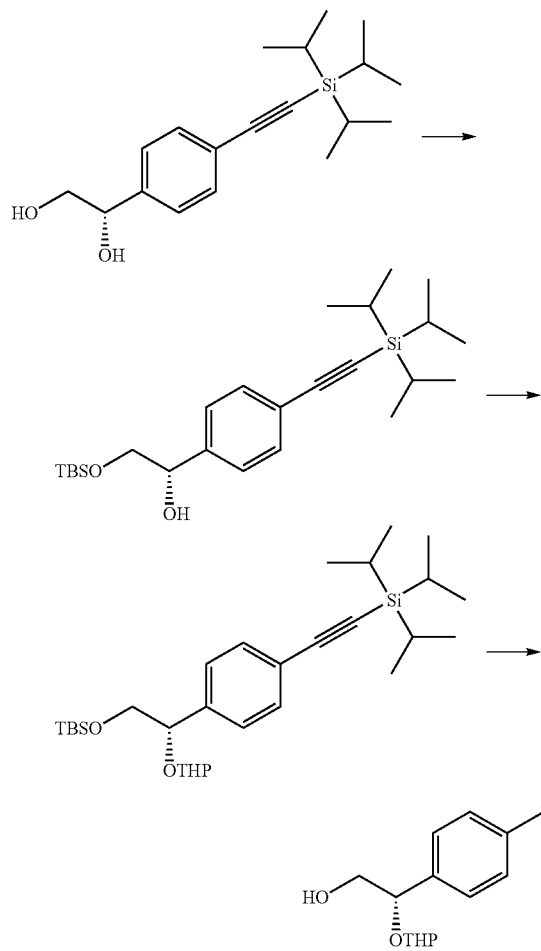

To a mixture of 2.79 g of (1S)-1-(4-((triisopropylsilyl)ethynyl)phenyl)ethane-1,2-diol, 28 mL of dichloromethane, 2.7 mL of triethylamine, and 213 mg of N,N-dimethylaminopyridine obtained in the same manner as in Production Example 3, 1.45 g of tert-butyldimethylsilyl chloride was added under a nitrogen atmosphere and under ice cooling, and the resulting mixture was stirred at room temperature for 2 hours, and then was allowed to stand at the same temperature overnight. A saturated aqueous solution of ammonium chloride and ethyl acetate were added to the reaction mixture, and the pH was adjusted to 4.0 with 6 mol/L hydrochloric acid. The organic layer was separated, washed with a saturated aqueous solution of sodium chloride, and then dried over anhydrous magnesium sulfate. The solvent was distilled off under reduced pressure to obtain 3.70 g of a brown oil.

To 3.70 g of the obtained brown oil, 28 mL of dichloromethane and 439 mg of pyridinium p-toluenesulfonate were added, 2.4 mL of 3,4-dihydro-2H-pyran was added under ice cooling, and then the resulting mixture was stirred at room temperature for 5 hours. To the reaction mixture, 3.0 mL of triethylamine was added, and the solvent was distilled off under reduced pressure. Water and ethyl acetate were added to the obtained residue. The organic layer was separated, washed with a saturated aqueous solution of sodium chloride, and then dried over anhydrous magnesium sulfate. The solvent was distilled off under reduced pressure, and the obtained residue was purified by silica gel column chromatography [eluent; diethyl ether:hexane=10:90] to obtain 3.65 g of a yellow oil.

To 3.65 g of the obtained yellow oil, 18 mL of tetrahydrofuran was added, then 17 mL of a 1 mol/L solution of tetra-n-butylammonium fluoride in tetrahydrofuran was added under ice cooling, and the resulting mixture was stirred at room temperature for 1 hour. A saturated aqueous solution of ammonium chloride and ethyl acetate were added to the reaction mixture. The organic layer was separated, washed with a saturated aqueous solution of sodium chloride, and then dried over anhydrous sodium sulfate. The solvent was distilled off under reduced pressure, and the obtained residue was purified by silica gel column chromatography [eluent; ethyl acetate:hexane=30:70-40:60] to obtain 1.78 g of (2S)-2-(4-ethynylphenyl)-2-(tetrahydro-2H-pyran-2-yloxy)ethanol as a white solid.

$^1$H-NMR (400 MHz, CDCl$_3$) δ: 1.40-1.93 (6H, m), 2.11-2.20 (1H, m), [3.06], 3.07 (1H, s), 3.51-3.61 (1H, m), 3.62-3.76 (2H, m), [3.25-3.34], 3.92-4.07 (1H, m), [4.48-4.53], 4.79-4.86 (1H, m), [4.70-4.75], 4.87-4.93 (1H, m), [7.29], 7.35 (2H, d, J=8.3 Hz), 7.45 (2H, d, J=8.0 Hz)

Production Example 10

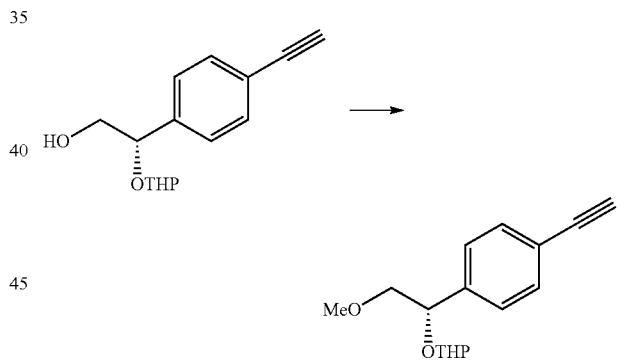

To a mixture of 800 mg of (2S)-2-(4-ethynylphenyl)-2-(tetrahydro-2H-pyran-2-yloxy)ethanol, 4.0 mL of dimethyl sulfoxide, and 0.4 mL of methyl iodide, 545 mg of potassium hydroxide was added under a nitrogen atmosphere and under ice cooling, and the resulting mixture was stirred at room temperature for 1 hour and 30 minutes. Toluene and a saturated aqueous solution of ammonium chloride were added to the reaction mixture, and the pH was adjusted to 6.1 with 6 mol/L hydrochloric acid. The organic layer was separated, washed with a saturated aqueous solution of sodium chloride, and then dried over anhydrous magnesium sulfate. The solvent was distilled off under reduced pressure, and the obtained residue was purified by silica gel column chromatography [eluent; ethyl acetate:hexane=10:90] to obtain 836 mg of 2-((1S)-1-(4-ethynylphenyl)-2-methoxyethoxy)tetrahydro-2H-pyran as a colorless oil.

$^1$H-NMR (400 MHz, CDCl$_3$) δ: 1.40-1.94 (6H, m), [3.05], 3.07 (1H, s), [3.36], 3.39 (3H, s), 3.45-3.56 (2H, m),

[3.56-3.62], 3.62-3.69 (1H, m), [3.28-3.35], 3.97-4.06 (1H, m), [4.80-4.85], 4.91-4.97 (1H, m), [4.41-4.46], 4.97-5.01 (1H, m), [7.30], 7.37 (2H, d, J=8.4 Hz), 7.44-7.51 (2H, m)

Production Example 11

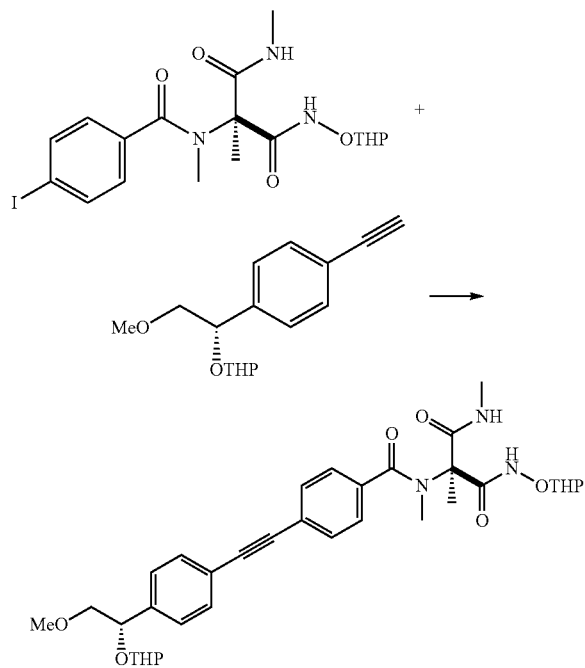

To a mixture of 478 mg of 2-((1S)-1-(4-ethynylphenyl)-2-methoxyethoxy)tetrahydro-2H-pyran, 3.0 mL of tetrahydrofuran, 300 mg of (2S)-2-((4-iodobenzoyl)(methyl)amino)-N,2-dimethyl-N'-(tetrahydro-2H-pyran-2-yloxy)malonamide, 43 mg of bis-triphenylphosphinepalladium(II) dichloride, and 23 mg of copper(I) iodide, 0.51 mL of triethylamine was added under a nitrogen atmosphere and under ice cooling, and the resulting mixture was stirred at the same temperature for 2 hours and 30 minutes. A saturated aqueous solution of ammonium chloride and ethyl acetate were added to the reaction mixture, and the pH was adjusted to 6.0 with 6 mol/L hydrochloric acid. The organic layer was separated, washed with a saturated aqueous solution of sodium chloride, and then dried over anhydrous magnesium sulfate. The solvent was distilled off under reduced pressure, and the obtained residue was purified by silica gel column chromatography [eluent; acetone:chloroform=10:90] to obtain 485 mg of (2S)-2-((4-((4-((1S)-2-methoxy-1-(tetrahydro-2H-pyran-2-yloxy)ethyl)phenyl)ethynyl)benzoyl)(methyl)amino)-N,2-dimethyl-N'-(tetrahydro-2H-pyran-2-yloxy)malonamide as a brown foamy solid.

$^1$H-NMR (400 MHz, CDCl$_3$) δ: 1.42-1.94 (12H, m), [1.81], 1.82 (3H, s), [2.85], 2.86 (3H, d, J=4.4 Hz), [3.17], 3.20 (3H, s), [3.37], 3.40 (3H, s), 3.47-3.72 (4H, m), [3.29-3.36], 3.83-3.91 (1H, m), 3.97-4.07 (1H, m), [4.43-4.48], 4.93-4.98 (1H, m), [4.84], 4.95 (1H, dd, J=7.3, 4.2 Hz), 4.98-5.03 (1H, m), [7.34], 7.41 (2H, d, J=8.3 Hz), 7.44-7.61 (6H, m), [6.96-7.04], 7.62-7.72 (1H, m), [10.01], 10.53 (1H, s)

Production Example 12

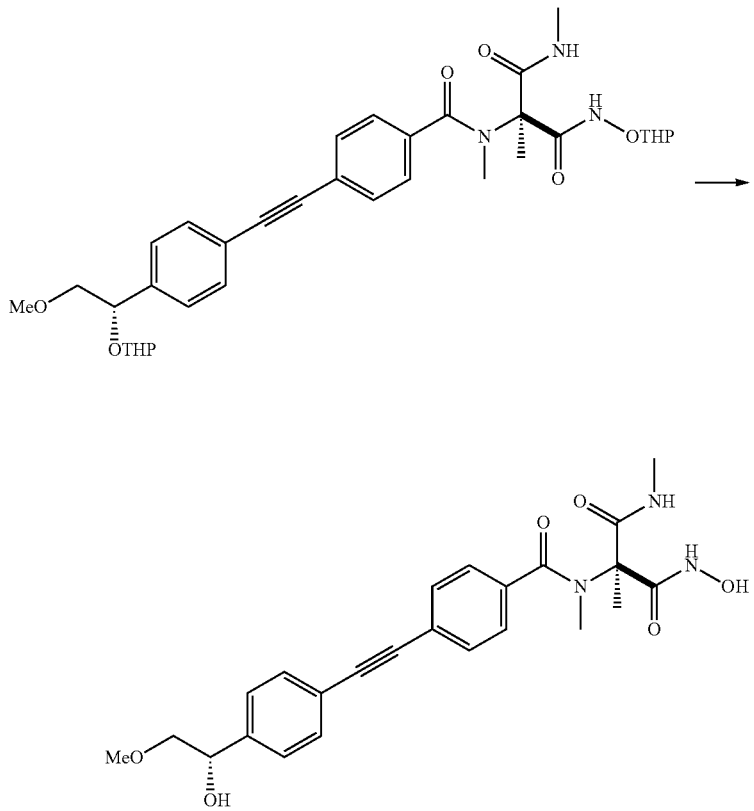

To a mixture of 485 mg of (2S)-2-((4-((4-((1S)-2-methoxy-1-(tetrahydro-2H-pyran-2-yloxy)ethyl)phenyl)ethynyl)benzoyl)(methyl)amino)-N,2-dimethyl-N'-(tetrahydro-2H-pyran-2-yloxy)malonamide and 4.8 mL of methanol, 23 mg of p-toluenesulfonic acid monohydrate was added under ice cooling, and the resulting mixture was stirred at the same temperature for 10 minutes and then at room temperature for 1 hour. Water and ethyl acetate were added to the reaction mixture, and the resulting mixture was neutralized with a saturated aqueous solution of sodium hydrogen carbonate. The organic layer was separated, and the obtained aqueous layer was extracted with ethyl acetate. Sodium chloride was added to the aqueous layer, and the aqueous layer was extracted with ethyl acetate twice. The organic layer was combined with the extract, and then dried over anhydrous sodium sulfate. The solvent was distilled off under reduced pressure, and the obtained residue was purified by silica gel column chromatography [eluent; methanol: chloroform=4:96-6:94] to obtain 288 mg of a brown solid. Ethyl acetate and IPE were added thereto, and the solid material was collected by filtration to obtain 240 mg of (2S)-N-hydroxy-2-((4-((4-((1S)-1-hydroxy-2-methoxyethyl)phenyl)ethynyl)benzoyl)(methyl)amino)-N',2-dimethyl-malonamide (Compound C) as a brown solid.

$^1$H-NMR (400 MHz, CD$_3$OD) δ: 1.77 (3H, s), 2.79 (3H, s), 3.17 (3H, s), 3.37 (3H, s), 3.50 (2H, d, J=5.9 Hz), 7.41 (2H, d, J=8.3 Hz), 7.47-7.65 (6H, m); MS (ESI): 476[M+Na]$^+$, 452[M-H]$^-$

EXAMPLE 1

To a solution of 72.0 g of HPβCD (HPB-EC, NIHON SHOKUHIN KAKO CO., LTD.) in 130 mL of water for injection, 7.2 g of Compound A monohydrate was added, and then stirred at room temperature to obtain an aqueous solution of Compound A. To this solution, a portion of water for injection was added to achieve a total amount of 200 mL. The resultant was filtered through a 0.22 μm membrane filter to obtain a liquid formulation. The liquid formulation had a pH of 4.5.

EXAMPLE 2

To 10 mL of the liquid formulation obtained in Example 1, 50 μL of 0.1 mol/L hydrochloric acid and 250 μL of 0.01 mol/L hydrochloric acid were added. The resultant was filtered through a 0.22 μm membrane filter to obtain a liquid formulation. The liquid formulation had a pH of 3.0.

EXAMPLE 3

To 10 mL of the liquid formulation obtained in Example 1, 70 μL of 0.01 mol/L hydrochloric acid was added. The resultant was filtered through a 0.22 μm membrane filter to obtain a liquid formulation. The liquid formulation had a pH of 4.0.

EXAMPLE 4

To 10 mL of the liquid formulation obtained in Example 1, 20 μL of a 0.01 mol/L sodium hydroxide aqueous solution was added. The resultant was filtered through a 0.22 μm membrane filter to obtain a liquid formulation. The liquid formulation had a pH of 5.1.

EXAMPLE 5

To 10 mL of the liquid formulation obtained in Example 1, 160 μL of a 0.01 mol/L sodium hydroxide aqueous solution was added. The resultant was filtered through a 0.22 μm membrane filter to obtain a liquid formulation. The liquid formulation had a pH of 6.0.

EXAMPLE 6

To 10 mL of the liquid formulation obtained in Example 1, 90 μL of a 0.1 mol/L sodium hydroxide aqueous solution and 50 μL of a 0.01 mol/L sodium hydroxide aqueous solution were added. The resultant was filtered through a 0.22 μm membrane filter to obtain a liquid formulation. The liquid formulation had a pH of 7.0.

EXAMPLE 7

To 10 mL of the liquid formulation obtained in Example 1, 60 μL of a 1 mol/L sodium hydroxide aqueous solution and 80 μL of a 0.1 mol/L sodium hydroxide aqueous solution were added. The resultant was filtered through a 0.22 μm membrane filter to obtain a liquid formulation. The liquid formulation had a pH of 8.0.

EXAMPLE 8

To 10 mL of the liquid formulation obtained in Example 1, 40 μL of a 10% citric acid monohydrate aqueous solution was added. The resultant was filtered through a 0.22 μm membrane filter to obtain a liquid formulation. The liquid formulation had a pH of 3.0.

EXAMPLE 9

To 10 mL of the liquid formulation obtained in Example 1, 2 μL of a 10% citric acid monohydrate aqueous solution was added. The resultant was filtered through a 0.22 μm membrane filter to obtain a liquid formulation. The liquid formulation had a pH of 3.9.

EXAMPLE 10

To 10 mL of the liquid formulation obtained in Example 1, 5 μL of a 1% meglumine aqueous solution was added. The resultant was filtered through a 0.22 μm membrane filter to obtain a liquid formulation. The liquid formulation had a pH of 5.1.

EXAMPLE 11

To 10 mL of the liquid formulation obtained in EXAMPLE 1, 25 μL of a 1% meglumine aqueous solution was added. The resultant was filtered through a 0.22 μm membrane filter to obtain a liquid formulation. The liquid formulation had a pH of 5.9.

EXAMPLE 12

To 10 mL of the liquid formulation obtained in EXAMPLE 1, 20 μL of a 10% meglumine aqueous solution was added. The resultant was filtered through a 0.22 μm membrane filter to obtain a liquid formulation. The liquid formulation had a pH of 6.9.

EXAMPLE 13

To 10 mL of the liquid formulation obtained in EXAMPLE 1, 19 mg of meglumine was added and stirred.

The resultant was then filtered through a 0.22 μm membrane filter to obtain a liquid formulation. The liquid formulation had a pH of 8.0.

EXAMPLE 14

To a solution of 14.4 g of HPβCD (HPB-EC, NIHON SHOKUHIN KAKO CO., LTD.) in 25 mL of water for injection, 1.44 g of Compound A monohydrate was added, and then stirred at room temperature to obtain an aqueous solution of Compound A. To this solution, a portion of water for injection was added to achieve a total amount of 40 mL. The resultant was filtered through a 0.22 μm membrane filter to obtain a preparation. To 5 mL of this preparation, a portion of 5% glucose aqueous solution (Otsuka Glucose Injection 5%, Otsuka Pharmaceutical Factory, Inc.) was added to achieve a total amount of 100 mL. This preparation was frozen at −78° C. to obtain a frozen liquid formulation.

EXAMPLE 15

To 10 mL of the preparation obtained in EXAMPLE 14, a 5% glucose aqueous solution (Otsuka Glucose Injection 5%, Otsuka Pharmaceutical Factory, Inc.) was added to achieve a total amount of 100 mL. This preparation was frozen at −78° C. to obtain a frozen liquid formulation.

EXAMPLE 16

To 20 mL of the preparation obtained in EXAMPLE 14, a portion of 5% glucose aqueous solution (Otsuka Glucose Injection 5%, Otsuka Pharmaceutical Factory, Inc.) was added to achieve a total amount of 100 mL. This preparation was frozen at −78° C. to obtain a frozen liquid formulation.

EXAMPLE 17

To a solution of 115.0 g of HPβCD (HPB-EC, NIHON SHOKUHIN KAKO CO., LTD.) in 200 mL of water for injection, 11.5 g of Compound A monohydrate was added and then, stirred at room temperature to obtain an aqueous solution of Compound A. To this solution, a portion of water for injection was added to achieve a total amount of 320 mL. The resultant was filtered through a 0.22 μm membrane filter to obtain a liquid preparation. Two mL of this preparation was filled into a vial, and lyophilized. Then, the vial was hermetically sealed to obtain a lyophilized formulation.

EXAMPLE 18

To 23 mL of the liquid preparation obtained in EXAMPLE 17, 2.31 g of D-mannitol was added, and stirred. Then, the resultant was filtered through a 0.22 μm membrane filter to obtain a liquid preparation. Two mL of this preparation was filled into a vial, and lyophilized. Then, the vial was hermetically sealed to obtain a lyophilized formulation.

EXAMPLE 19

To 23 mL of the liquid preparation obtained in EXAMPLE 17, 2.31 g of D-sorbitol was added, and stirred. Then, the resultant was filtered through a 0.22 μm membrane filter to obtain a liquid preparation. Two mL of this preparation was filled into a vial, and lyophilized. Then, the vial was hermetically sealed to obtain a lyophilized formulation.

EXAMPLE 20

To 23 mL of the liquid preparation obtained in EXAMPLE 17, 2.31 g of xylitol was added, and stirred. Then, the resultant was filtered through a 0.22 μm membrane filter to obtain a liquid preparation. Two mL of this preparation was filled into a vial, and lyophilized. Then, the vial was hermetically sealed to obtain a lyophilized formulation.

EXAMPLE 21

To 23 mL of the preparation obtained in EXAMPLE 17, 2.30 g of trehalose was added, and stirred. Then, the resultant was filtered through a 0.22 μm membrane filter to obtain a liquid preparation. Two mL of this preparation was filled into a vial, and lyophilized. Then, the vial was hermetically sealed to obtain a lyophilized formulation.

EXAMPLE 22

To 23 mL of the liquid preparation obtained in EXAMPLE 17, 2.29 g of glucose was added, and stirred. Then, the resultant was filtered through a 0.22 μm membrane filter to obtain a liquid preparation. Two mL of this preparation was filled into a vial, and lyophilized. Then, the vial was hermetically sealed to obtain a lyophilized formulation.

EXAMPLE 23

To 23 mL of the liquid preparation obtained in EXAMPLE 17, 2.31 g of fructose was added, and stirred. Then, the resultant was filtered through a 0.22 μm membrane filter to obtain a liquid preparation. Two mL of this preparation was filled into a vial, and lyophilized. Then, the vial was hermetically sealed to obtain a lyophilized formulation.

EXAMPLE 24

To 23 mL of the liquid preparation obtained in EXAMPLE 17, 2.30 g of sucrose was added, and stirred. Then, the resultant was filtered through a 0.22 μm membrane filter to obtain a liquid preparation. Two mL of this preparation was filled into a vial, and lyophilized. Then, the vial was hermetically sealed to obtain a lyophilized formulation.

EXAMPLE 25

To 23 mL of the liquid preparation obtained in EXAMPLE 17, 2.29 g of glycine was added, and stirred. Then, the resultant was filtered through a 0.22 μm membrane filter to obtain a liquid preparation. Two mL of this preparation was filled into a vial, and lyophilized. Then, the vial was hermetically sealed to obtain a lyophilized formulation.

EXAMPLE 26

To 24 mL of the liquid preparation obtained in the same manner as in Example 17, 40 μL of a 0.01 mol/L sodium hydroxide aqueous solution was added. This aqueous solution had a pH of 5.0. This aqueous solution was filtered through a 0.22 μm membrane filter to obtain a liquid preparation. Two mL of this preparation was filled into a vial, and lyophilized. Then, the vial was hermetically sealed to obtain a lyophilized formulation.

EXAMPLE 27

To 24 mL of the liquid preparation obtained in the same manner as in Example 17, 100 μL of a 0.1 mol/L sodium hydroxide aqueous solution, 40 μL of a 0.01 mol/L sodium hydroxide aqueous solution and 95 μL of 0.1 mol/L hydrochloric acid were added. This aqueous solution had a pH of 5.0. This aqueous solution was filtered through a 0.22 μm membrane filter to obtain a liquid preparation. Two mL of this preparation was filled into a vial, and lyophilized. Then, the vial was hermetically sealed to obtain a lyophilized formulation.

EXAMPLE 28

To 24 mL of the liquid preparation obtained in the same manner as in Example 17, 10 μL of a 1% meglumine aqueous solution was added. This aqueous solution had a pH of 5.0. This aqueous solution was filtered through a 0.22 μm membrane filter to obtain a liquid preparation. Two mL of this preparation was filled into a vial, and lyophilized. Then, the vial was hermetically sealed to obtain a lyophilized formulation.

EXAMPLE 29

To 24 mL of the liquid preparation obtained in the same manner as in Example 17, 20 μL of a 10% meglumine aqueous solution, 5 μL of a 1% meglumine aqueous solution and μL of 0.1 mol/L hydrochloric acid were added. This aqueous solution had a pH of 5.0. This aqueous solution was filtered through a 0.22 μm membrane filter to obtain a liquid preparation. Two mL of this preparation was filled into a vial, and lyophilized. Then, the vial was hermetically sealed to obtain a lyophilized formulation.

EXAMPLE 30

To 10 mL of the liquid formulation obtained in EXAMPLE 1, 50 μL of 1 mol/L hydrochloric acid and 350 μL of 0.1 mol/L hydrochloric acid were added to obtain a liquid formulation. The liquid formulation had a pH of 2.0.

EXAMPLE 31

To 10 mL of the liquid formulation obtained in EXAMPLE 1, 300 μL of a 1 mol/L sodium hydroxide aqueous solution was added to obtain a liquid formulation. The liquid formulation had a pH of 9.0.

EXAMPLE 32

To 10 mL of the liquid formulation obtained in EXAMPLE 1, 20 mg of citric acid monohydrate and 225 μL of a 10% citric acid monohydrate aqueous solution were added to obtain a liquid formulation. The liquid formulation had a pH of 2.0.

EXAMPLE 33

To 10 mL of the liquid formulation obtained in Example 1, 100 mg of meglumine was added to obtain a liquid formulation. The liquid formulation had a pH of 9.0.

EXAMPLES 34 to 75

In accordance with the following experimental procedures, liquid formulations of Examples 34 to 75 were obtained.

Each abbreviation in tables has the following meaning.
Ac-L-Trp-OH: N-acetyl-L-tryptophan
Ala: Alanine
Arg: Arginine
BnOH: Benzyl alcohol
DMAc: N,N-dimethylacetamide
DMSO: Dimethylsulfoxide
EtOH: Ethanol
His: Histidine
L-Phe-OBu(t)HCl: L-phenylalanine tert-butyl ester hydrochloride
PEG: Polyethylene glycol
Phe: Phenylalanine
Pro: Proline
Trp: Tryptophan
β-Ala-OBu(t)HCl: β-alanine tert-butyl ester hydrochloride
Experimental Procedure A
Compound A monohydrate, saline or water for injection, and a solubilizing agent, were mixed and then, stirred at room temperature to obtain a liquid formulation. When this liquid formulation was allowed to stand at room temperature for 2 hours, no precipitate was observed.
Experimental Procedure B
Compound A monohydrate, saline or water for injection, and a solubilizing agent, were mixed and ultrasonicated to be dispersed. This mixture was warmed to 40 to 50° C. to dissolve Compound A monohydrate, and then, left to room temperature to obtain a liquid formulation. When this liquid formulation was allowed to stand at room temperature for 2 hours, no precipitate was observed.

TABLE 1

Water for injection, Compound A monohydrate

| | | Example | | | | | | |
|---|---|---|---|---|---|---|---|---|
| | | 34 | 35 | 36 | 37 | 38 | 39 | 40 |
| | | Experimental procedure | | | | | | |
| | | A | A | A | A | B | B | B |
| Compound A monohydrate | (mg) | 20 | 20 | 40 | 40 | 61 | 63 | 61 |
| Saline | (mL) | 1 | 1 | 1 | 1 | | | |
| Water for injection | (mL) | | | | | 1.2 | 1.2 | 1.2 |
| BnOH | (mL) | | | 0.3 | 0.2 | | | |
| EtOH | (mL) | | | 0.5 | | | 0.3 | |
| DMAc | (mL) | | | | 0.5 | 0.6 | 0.3 | 0.6 |
| PEG400 | (mL) | | | | | 1.2 | 1.2 | |
| Triethylene glycol | (mL) | | | | | | | 1.2 |
| L-Arg | (mg) | 140 | | | | | | |
| Trometamol | (mg) | | 600 | | | | | |

TABLE 2

Water for injection, Compound A monohydrate

| | | Example | | | | | |
|---|---|---|---|---|---|---|---|
| | | 41 | 42 | 43 | 44 | 45 | 46 |
| | | Experimental procedure | | | | | |
| | | B | A | A | A | A | A |
| Compound A monohydate | (mg) | 61 | 40 | 40 | 40 | 40 | 40 |
| Saline | (mL) | | 1 | 1 | 1 | 1 | 1 |
| Water for injection | (mL) | 1.2 | | | | | |
| BnOH | (mL) | | 0.4 | 0.02 | | | |
| EtOH | (mL) | 0.3 | | | | | |
| DMAc | (mL) | 0.3 | | 0.65 | 0.68 | 0.25 | |
| PEG400 | (mL) | | 0.6 | | | | |
| Triethylene glycol | (mL) | 1.2 | | | | | |
| DMSO | (mL) | | | | | | 0.6 |
| Meglumine | (mg) | | | 17.2 | 17.3 | | |
| NaOH | (mg) | | | | | 3.6 | 3.6 |

TABLE 3

Water for injection, Compound A monohydrate

| | | Example | | | | | | | |
|---|---|---|---|---|---|---|---|---|---|
| | | 47 | 48 | 49 | 50 | 51 | 52 | 53 | 54 |
| | | Experimental procedure | | | | | | | |
| | | A | A | A | A | A | A | A | A |
| Compound A monohydrate | (mg) | 40 | 40 | 40 | 40 | 40 | 40 | 40 | 40 |
| Saline | (mL) | 1 | 1 | 1 | 1 | 1 | 1 | 1 | 1 |
| Water for injection | (mL) | | | | | | | | |
| EtOH | (mL) | | | | | | | | |
| DMAc | (mL) | 0.9 | 0.5 | 0.6 | 0.95 | 0.6 | 0.9 | 0.9 | 0.9 |
| PEG400 | (mL) | | | | | | | | |
| Meglumine | (mg) | 17.2 | 34.6 | 17.2 | 17.2 | 17.2 | | | |
| Benzoic acid | (mg) | 10.7 | 2.4 | | | | | | |
| Sodium benzoate | (mg) | | | 12.7 | | | | 12.6 | |
| Citric acid | (mg) | | | | 18.7 | | | | |
| Sodium citrate | (mg) | | | | | | | | 25.8 |
| Nicotinic acid amide | (mg) | | | | | | 10.8 | 10.7 | |

TABLE 4

Water for injection, Compound A monohydrate

| | | Example | | | | | |
|---|---|---|---|---|---|---|---|
| | | 55 | 56 | 57 | 58 | 59 | 60 |
| | | Experimental procedure | | | | | |
| | | A | B | B | B | B | B |
| Compound A monohydrate | (mg) | 40 | 20 | 20 | 21 | 20 | 21 |
| Saline | (mL) | 1 | 0.7 | | | | |
| Water for injection | (mL) | | | 0.5 | 0.4 | 0.7 | 0.6 |
| EtOH | (mL) | | | | 0.2 | | |
| DMAc | (mL) | 0.9 | 0.3 | 0.1 | | 0.3 | 0.4 |
| PEG400 | (mL) | | | 0.4 | 0.4 | | |
| Benzoic acid | (mg) | | 70 | | | | |
| Sodium lactate | (mg) | 26.3 | | | | | |
| Nicotinic acid amide | (mg) | | | 203 | 206 | 206 | 121 |

TABLE 5

Compound A monohydrate

| | | Example | | | | | | | |
|---|---|---|---|---|---|---|---|---|---|
| | | 61 | 62 | 63 | 64 | 65 | 66 | 67 | 68 |
| | | Experimental procedure | | | | | | | |
| | | A | A | A | A | A | A | A | A |
| Compound A monohydrate | (mg) | 40 | 40 | 40 | 40 | 40 | 40 | 40 | 40 |
| Saline | (mL) | 1 | 1 | 1 | 1 | 1 | 1 | 1 | 1 |
| DMAc | (mL) | 0.9 | 0.9 | 0.9 | 0.9 | 0.9 | 0.9 | 0.9 | 0.9 |
| L-His | (mg) | 13.7 | | | | | | | |
| L-Phe | (mg) | | 14.7 | | | | | | |
| L-Trp | (mg) | | | 18.0 | | | | | |
| DL-Pro | (mg) | | | | 10.2 | | | | |
| β-Ala | (mg) | | | | | 7.9 | | | |
| D-Phe | (mg) | | | | | | 14.5 | | |
| D-Trp | (mg) | | | | | | | 17.9 | |
| Cinnamic acid | (mg) | | | | | | | | 13.1 |

TABLE 6

Compound A monohydrate

| | | Example | | | | | | |
|---|---|---|---|---|---|---|---|---|
| | | 69 | 70 | 71 | 72 | 73 | 74 | 75 |
| | | Experimental procedure | | | | | | |
| | | A | A | A | A | A | A | A |
| Compound A monohydrate | (mg) | 40 | 40 | 40 | 40 | 40 | 40 | 40 |
| Saline | (mL) | 1 | 1 | 1 | 1 | 1 | 1 | 1 |
| DMAc | (mL) | 0.9 | 0.9 | 0.9 | 0.9 | 0.9 | 0.9 | 0.9 |
| 3-Phenylpropionic acid | (mg) | 13.2 | | | | | | |
| 3-(4-Hydroxyphenyl)propionic acid | (mg) | | 14.7 | | | | | |
| Ac-L-Trp-OH | (mg) | | | 21.6 | | | | |
| β-Ala-OBu(t)HCl | (mg) | | | | 15.9 | | | |

TABLE 6-continued

Compound A monohydrate

| | Example | | | | | | |
|---|---|---|---|---|---|---|---|
| | 69 | 70 | 71 | 72 | 73 | 74 | 75 |
| | Experimental procedure | | | | | | |
| | A | A | A | A | A | A | A |
| L-Phe-OBu(t)HCl (mg) | | | | 22.6 | | | |
| Taurine (mg) | | | | | | 11.0 | |
| p-Toluenesulfonic acid monohydrate (mg) | | | | | | | 16.9 |

Test Example 1 Test to Evaluate *Pseudomonas aeruginosa* LpxC Enzyme Inhibitory Activity Compound A, Compound B and Compound C were used as a test compound.

The *Pseudomonas aeruginosa* LpxC enzyme activity was measured by reacting LpxC with its substrate UDP-3-O-R-3-hydroxydecanoyl)-N-acetylglucosamine and measuring the amount of the reaction product by the quantification of an amino group present in the product. This measurement was carried out according to a method described in, for example, International Publication No. WO 11/132712 pamphlet or a method similar thereto.

Specifically, to the *Pseudomonas aeruginosa* LpxC enzyme (which was obtained by preparing chromosomal DNA from *Pseudomonas aeruginosa*, obtaining the *Pseudomonas aeruginosa* LpxC gene by PCR (polymerase chain reaction) using LpxC-specific primers, and incorporating this gene into a vector, followed by gene expression using *Escherichia coli*), 20 µmol/L UDP-3-O-(R-3-hydroxydecanoyl)-N-acetylglucosamine (Wako Pure Chemical Industries, Ltd.) was added, and the mixture was incubated at 25° C. for 1 hour. This reaction was carried out in a 40 mmol/L HEPES buffer solution (pH 8.0) containing 0.02% Brij 35 and 80 µmol/L dithiothreitol. The reaction was terminated by the addition of 20% acetic acid (final concentration: 0.95%) to the reaction solution. Then, fluorescamine (final concentration: 1.6 µmg/mL) dissolved in anhydrous dioxane was added thereto. The amount of the reaction product was detected at an excitation wavelength/fluorescence wavelength=390 nm/495 nm. Each test compound was allowed to coexist at various concentrations in the reaction to obtain an inhibition curve. From the inhibition curve, the concentration at which the test compound inhibited 50% of the amount of the reaction product ($IC_{50}$ value) was determined and used as an index for *Pseudomonas aeruginosa* LpxC enzyme inhibitory activity.

As a result, all the $IC_{50}$ values of the test compounds were less than 50 nM.

The test compounds exhibited an excellent *Pseudomonas aeruginosa* LpxC enzyme inhibitory activity.

Test Example 2 Test to Evaluate Antibacterial Activity

Compound A, Compound B and Compound C were used as a test compound.

The minimum inhibitory concentration (MIC) was measured according to the CLSI (Clinical and Laboratory Standards Institute) standard method using a broth microdilution method given below.

The bacteria used were a *Pseudomonas aeruginosa* ATCC27853 strain.

Test bacterial cells of each strain cultured overnight in a Mueller-Hinton agar medium were scraped off and suspended at the McFarland 0.5 standard, and this suspension was diluted 10-fold to prepare an inoculum solution. The inoculum solution (0.005 mL) was inoculated to a cation-adjusted Mueller-Hinton medium containing each test compound and cultured at 35° C. for 16 to 20 hours. The minimum drug concentration at which bacterial growth was not visible to the naked eye was defined as MIC.

As a result, all the MICs of the test compounds were 1 µg/mL.

The test compounds exhibited an excellent antimicrobial activity against *Pseudomonas aeruginosa*.

Test Example 3 Test on Defense Against Mouse Systemic Infection Using *Pseudomonas aeruginosa*

Compound A and Compound B were used as a test compound.

The mice used were male ICR SPF mice (4 weeks old: 5 individuals per group).

To prepare a bacterial inoculum solution, a *Pseudomonas aeruginosa* clinical isolate (S-3232 strain) cultured overnight at 37° C. on a Mueller-Hinton agar plate was cultured for 4 hours in a cation-adjusted Mueller-Hinton medium and then diluted 10-fold with a 10% mucin/phosphate buffer solution to prepare the inoculum solution.

Infection was induced by the intraperitoneal inoculation of 0.5 mL of the inoculum solution (approximately $10^4$ CFU/mouse) to each mouse. Each test compound was dissolved in a 10% HPβCD/2.5% mannitol aqueous solution and subcutaneously administered a single dose of 12.5 mg/kg at 1 hour after the infection. Three days after the infection, the number of survivors was recorded.

As a result, in the control group wherein the test compound was not administered, all the mice died. In the groups wherein the test compound was administered, 80% or more of the mice were observed to survive 3 days after the bacterial inoculation, and an in vivo anti-*Pseudomonas aeruginosa* activity was confirmed. Also, in the group wherein 6.25 mg/kg of the test compound was administered, 80% or more of the mice were observed to survive 3 days after the bacterial inoculation, and an excellent in vivo anti-*Pseudomonas aeruginosa* activity was confirmed.

Test Example 4 Test on Defense Against Mouse Systemic Infection Using Multidrug-resistant *Pseudomonas aeruginosa*

Compound A, Compound B and Compound C were used as a test compound.

The mice used were male ICR SPF mice (4 weeks old: 5 individuals per group).

To prepare a bacterial inoculum solution, a multidrug-resistant *Pseudomonas aeruginosa* clinical isolate (S-2838 strain) cultured overnight at 37° C. on a Mueller-Hinton agar plate was cultured for 5 hours in a cation-adjusted Mueller-Hinton medium and then diluted 10-fold with a 10% mucin/phosphate buffer solution to prepare the inoculum solution.

Infection was induced by the intraperitoneal inoculation of 0.5 mL of the inoculum solution (approximately $10^6$ CFU/mouse) to each mouse. Each test compound was dissolved in a 10% HPβCD/2.5% mannitol aqueous solution and intravenously administered to the tail a single dose of 50 mg/kg at 1 hour after the infection. Three days after the infection, the number of survivors was recorded.

As a result, in the control group wherein the test compound was not administered, all the mice died. In all the groups wherein the test compound was administered, 100% of the mice were observed to survive 3 days after the bacterial inoculation, and an in vivo anti-multidrug-resistant *Pseudomonas aeruginosa* activity was confirmed. Also, in the group wherein 25 mg/kg of Test Compound A was administered, 60% or more of the mice were observed to survive 3 days after the bacterial inoculation, and an excellent in vivo anti-multidrug-resistant *Pseudomonas aeruginosa* activity was confirmed.

Test Example 5 Test on Mouse Model with Urinary Tract Infection by Multidrug-resistant *Pseudomonas aeruginosa*

Compound A, Compound B and Compound C were used as a test compound.

The mice used were female ICR SPF mice (5 weeks old: 5 individuals per group).

To prepare a bacterial inoculum solution, a *Pseudomonas aeruginosa* clinical isolate (S-2838 strain) was suspended in sterile saline.

Infection was induced by the inoculation of 0.2 mL of the inoculum solution (approximately $10^3$ CFU/mouse) through the urethra of each mouse. Each test compound was dissolved in a 10% HPβCD/2.5% mannitol aqueous solution and intravenously administered to the tail at a dose of 25 mg/kg once 2 hours after the infection. The numbers of bacterial colonies of the next day of the infection in the kidneys were recorded, and an average thereof was calculated.

As a result, in all the groups wherein the test compound was administered, as compared to the control group wherein the test compound was not administered, a decrease of 2 log CFU/kidney or more in the intrarenal viable cell count was observed, and an anti-*Pseudomonas aeruginosa* activity in the urinary tract infection model was confirmed. Also, in the group wherein 12.5 mg/kg of Test Compound A was administered, as compared to the control group wherein the test compound was not administered, a decrease of 2 log CFU/kidney or more in the intrarenal viable cell count was observed, and an excellent anti-*Pseudomonas aeruginosa* activity in the urinary tract infection model was confirmed.

Test Example 6 Test on Mouse Model with Pulmonary Infection by Multidrug-resistant *Pseudomonas aeruginosa*

Compound A, Compound B and Compound C were used as a test compound.

The mice used were male ICR SPF mice (4.5 weeks old at the time of infection: 5 individuals per group). In order to achieve a transient compromised state, cyclophosphamide was intraperitoneally administered at a dose of 200 mg/kg to each mouse 4 days before injection.

To prepare a bacterial inoculum solution, a *Pseudomonas aeruginosa* clinical isolate (S-2838 strain) was suspended in sterile saline.

Infection was induced by the inoculation of 0.05 mL of the inoculum solution (approximately $10^5$ CFU/mouse) to each mouse intranasally. Each test compound was dissolved in a 10% HPβCD/2.5% mannitol aqueous solution and intravenously administered to the tail at a dose of 50 mg/kg twice 2 and 8 hours after the infection. The numbers of bacterial colonies of the next day of the infection in the lungs were recorded, and an average thereof was calculated.

As a result, in all the groups wherein the test compound was administered, as compared to the control group wherein the test compound was not administered, a decrease of 2 log CFU/lung or more in the intrapulmonary viable cell count was observed, and an anti-*Pseudomonas aeruginosa* activity in the pulmonary infection model was confirmed. Also, in the group wherein 25 mg/kg of Test Compound A was administered, as compared to the control group wherein the test compound was not administered, a decrease of 2 log CFU/lung or more in the intrapulmonary viable cell count was observed, and an excellent anti-*Pseudomonas aeruginosa* activity in the pulmonary infection model was confirmed.

Test Example 7 Test on Inhibition of Vero Cell Growth

Compound A, Compound B and Compound C were used as a test compound.

Each test compound was dissolved in dimethyl sulfoxide, adjusted to each concentration using E'MEM, and then dispensed at 0.1 mL/well to 96-well microplates. The Vero cell suspension was prepared at $3\times10^4$ cells/mL using E'MEM supplemented with 20% FBS, inoculated thereto at 0.1 mL/well, and cultured at 37° C. for 3 days under 5% $CO_2$. At the completion of the culture, PBS supplemented with 1 mg/mL 2,3-bis-(2-methoxy-4-nitro-5-sulfophenyl)-5-((phenylamino)carbonyl)-2H-tetrazolium inner salt monosodium salt (XTT) and 25 μM phenazine methosulfate (PMS) was prepared and added thereto at 50 μL/well. Approximately 2 hours later, the absorbance at 450 nm was measured using a microplate reader.

The absorbance ratio between a test compound-non-supplemented control and each well was calculated to calculate the concentration at which the compound inhibited 50% of cell growth ($CC_{50}$; μg/mL).

As a result, all the $CC_{50}$s of the test compounds were 100 μg/mL or more.

Test Example 8 Evaluation of hERG Inhibitory Activity

Compound A and Compound C were used as a test compound.

HEK 293 cells (human embryo kidney 293 cells, Cytomyx LLC) transfected with hERG gene (human ether-a-go-go related gene) were used.

The culture solution used was a MEM medium containing 10% fetal bovine serum and 1% non-essential amino acid and further supplemented with Geneticin at a concentration of 400 jag/mL. The cells were cultured in a carbonic acid gas incubator (37.0° C., 5% $CO_2$).

The hERG current was measured by a whole cell clamp method. A glass cover with the cells for measurement attached thereto was placed in a dish and perfused at a rate of 2 mL/min with a perfusate (composition: 137 mmol/L NaCl, 4 mmol/L KCl, 10 mmol/L HEPES, 1.8 mmol/L $CaCl_2$, 1 mmol/L $MgCl_2$, 10 mmol/L glucose, pH 7.4). The inside temperature of the perfusion chamber was kept at 25° C. The cells were contacted with a glass electrode (2.0 to 8.0 MΩ) charged with an internal solution (composition: 130 mmol/L KCl, 1 mmol/L $MgCl_2$, 5 mmol/L EGTA, 10 mmol/L HEPES, 5 mmol/L MgATP, pH 7.2) to break the patch membranes, followed by the measurement of the hERG current using a patch clamp amplifier (EPC-7 Plus, HEKA) via patch clamp software pClamp 10 (Molecular Devices Corporation). The pulse protocol involved a holding potential of −80 mV, a depolarizing pulse of +20 mV for 1.5 seconds and a repolarizing pulse of −50 mV for 1.5 seconds. After confirmation that a stable current waveform was obtained, each test compound was applied thereto.

Before the application and 10 minutes after the application, the peak value of tail current in the hERG current waveform was analyzed to calculate the ratio of the value 10 minutes after the application to the value before the application (relative value, %).

As a result, none of the test compounds exhibited an hERG inhibitory activity up to 300 μmol/L.

Test Example 9 In Vitro Micronucleus Test for Examining the Presence or Absence of Genotoxicity Compound A was used as a test compound.

In order to examine the inducibility of the chromosomal aberrations by each test compound in cultured cells, the in vitro micronucleus test was carried out. This test was carried out by a short-time treatment method (in the presence and absence of a metabolic activation) and a 30-hour treatment method using Chinese hamster lung fibroblasts (CHL/IU cells). The concentration of the test compound was set to 1.00 mmol/L as the maximum dose with reference to the "Guidance on Genotoxicity Testing and Data Interpretation for Pharmaceuticals Intended for Human Use". Specimens were observed as to doses of 0.25, 0.50 and 1.00 mmol/L.

The cells were inoculated at $15 \times 10^4$ cells to a 60-mm dish (IWAKI) and precultured at 37° C. for 24 hours under 5% $CO_2$ using a MEM medium (Sigma-Aldrich Co., Ltd.) containing 10% newborn calf serum (Sigma-Aldrich Co., Ltd.) and 50 U/mL-50 µg/mL Penicillin-Streptomycin (Sigma-Aldrich Co., Ltd.). After the completion of the preculture, a vehicle (DMSO) or each test compound was added thereto. In the short-time treatment method, 6 hours after the culture, the cells were washed with PBS(−) (Sigma-Aldrich Co., Ltd.), and then, the medium was replaced with a fresh medium, followed by further culture for 24 hours. In the 30-hour treatment method, after the addition of the test compound, the cells were cultured for 30 hours. After the completion of the culture, the cells were dissociated using a 0.05% trypsin-EDTA solution (Sigma-Aldrich Co., Ltd.). After centrifugation, the supernatant was removed, and 3 mL of a 0.075 mol/L aqueous potassium chloride solution was added to the cells. After hypotonic treatment at room temperature for 5 minutes, the cells were fixed with an ice-cold fixing solution (methanol:acetic acid=19:1) to prepare a glass slide specimen (giemsa-stained (Merck)). Two thousand cells per dose were observed to measure the number of cells having the micronucleus. When the frequency of appearance of the micronucleus in the test compound group was significantly increased as compared with the vehicle control group, the test compound was confirmed to be positive. When this frequency of appearance was equivalent to that of the vehicle control, the test compound was confirmed to be negative.

As a result, in either treatment method, the test compound was negative at the dose of 1 mmol/L or less.

Test Example 10 Measurement of Binding Ratio to Plasma Protein

Compound A and Compound C were used as a test compound.

Each test compound was added to human serum to prepare a 1 µg/mL spiked serum, which was then left standing at room temperature for 1 hour or longer. A filtrate (20 µL) was collected by a centrifugal ultrafiltration method (molecular weight cutoff: 10,000, 1500×g, 25° C., 10 min), then human serum and an internal standard solution (furosemide-acetonitrile solution) were added thereto. To the compound-spiked serum, PBS and an internal standard solution were added. Each mixture was stirred and then centrifuged, and the concentration in the supernatant was determined by LC-MS/MS.

The ratio of protein binding was determined according to the following calculation expression:

Ratio of protein binding (%)=(1−(Concentration of the filtrate)/(Concentration of the compound-spiked serum))×100

As a result, all the protein binding ratios of the test compounds were 80% or less.

Test Example 11 Inhibitory Effect on Liver Drug-metabolizing Enzyme in Human

Compound A and Compound C were used as a test compound.

Pooled human liver microsomes were used. Substrates and their final concentrations as well as the positive controls and their final concentrations were as described in Tables 7 and 8. The reaction was carried out in a phosphate buffer solution (100 mmol/L, pH 7.4), and the final concentrations of the reaction system were set to 0.5 mg/mL human liver microsome protein, 1.55 mmol/L oxidized form of nicotinamide adenine dinucleotide phosphate (NADP+), 3.3 mmol/L glucose-6-phosphate, 3.3 mmol/L magnesium chloride and 0.4 Units/mL glucose-6-phosphate dehydrogenase (G6PDH). The final concentration of each compound in the reaction solution was set to 100 µM. Each of these reaction solutions was incubated at 37° C. for 30 minutes. Then, the substrates were added thereto and reacted at 37° C. for 10 minutes. The reaction was terminated by the addition of a 1.5-fold volume of an internal standard solution (acetonitrile solution containing 0.25 mmol/L dextrorphan and 2% formic acid). Then, the solution was centrifuged, and the concentration of metabolites in the supernatant was determined by LC-MS/MS.

The ratio of inhibitory activity by addition of the inhibitor was determined according to the following calculation expression:

Ratio of inhibitory activity (%)=(1−(Concentration of CYP metabolites in the presence of the test compound)/(Concentration of CYP metabolites in the absence of the test compound))×100

As a result, all the inhibitory activity ratios of the test compounds were 30% or less.

TABLE 7

| Molecular species | Substrate name | Final concentration (µmol/L) |
| --- | --- | --- |
| CYP1A2 | Phenacetin | 10 |
| CYP2C8 | Amodiaquine | 0.2 |
| CYP2C9 | Tolbutamide | 100 |
| CYP2C19 | (S)-Mephenytoin | 40 |
| CYP2D6 | (±)-Bufuralol | 4 |
| CYP3A4 | Midazolam | 1 |
| CYP3A4 | Testosterone | 5 |

TABLE 8

| Molecular species | Positive control | Final concentration (µmol/L) |
| --- | --- | --- |
| CYP1A2 | Furafyline | 10 |
| CYP2C8 | Quercetin | 10 |
| CYP2C9 | Tienilic acid | 1 |
| CYP2C19 | Ticlopidine | 1 |
| CYP2D6 | Paroxetine | 2 |
| CYP3A4 | Verapamil | 10 |

Test Example 12 Stability Test

The liquid formulations obtained in Examples 2 to 13 and 30 to 33 were stored at 25° C. for 24 hours. The concentration of Compound A after storage was measured by the HPLC method to determine the residual ratio.

The results are shown in Table 9.

The residual ratio was determined by the following expression.

Residual ratio (%)=(Concentration of Compound $A$ after storage/Concentration of Compound $A$ at the beginning of the test)×100

<HPLC Measurement Conditions>
Detector: LC-2010CHT (SHIMADZU CORPORATION)
Detection at: 254 nm
Column: XBridge C18 4.6×150 mm (Waters Corporation)

Precolumn: Develosil ODS-HG 4.0×10 mm (Nomura Chemical Co., Ltd.)

Column temperature: 40° C.

Flow rate: 1.0 mL/minute

Mobile phase A: water/(0.2 mol/L formate buffer solution (pH 3))=90/10

Mobile phase B: acetonitrile/(0.2 mol/L formate buffer solution (pH 3))=90/10

Gradient cycle: 0 min (A solution/B solution=90/10), 15 min (A solution/B solution=70/30), 20 min (A solution/B solution=0/100), 30 min (A solution/B solution=0/100)

TABLE 9

|  | pH | Residual ratio (%) |
|---|---|---|
| Example 2 | 3.0 | 96.9 |
| Example 3 | 4.0 | 99.4 |
| Example 4 | 5.1 | 100.0 |
| Example 5 | 6.0 | 99.4 |
| Example 6 | 7.0 | 98.8 |
| Example 7 | 8.0 | 97.8 |
| Example 8 | 3.0 | 97.6 |
| Example 9 | 3.9 | 99.7 |
| Example 10 | 5.1 | 101.9 |
| Example 11 | 5.9 | 100.4 |
| Example 12 | 6.9 | 98.2 |
| Example 13 | 8.0 | 101.0 |
| Example 30 | 2.0 | 93.0 |
| Example 31 | 9.0 | 92.6 |
| Example 32 | 2.0 | 93.5 |
| Example 33 | 9.0 | 92.1 |

The residual ratios of the liquid formulations in Examples were 90% or more. Particularly, the residual ratios of the liquid formulations in Examples in which the pH was from 3 to 8 were 95% or more. The liquid formulations in Examples were stable.

Test Example 13 Solubility Test

Compound A monohydrate was used as a test compound. To 5 mL of a 10% CD or CD derivative solution, about 100 mg of Compound A monohydrate was added, and stirred at room temperature for 24 hours. To the solutions in which αCD, HPαCD, DMβCD and methyl-β-cyclodextrin were used, about 100 mg of Compound A monohydrate was added after 6 hours. After centrifugation (3000 rpm, 10 minutes), the supernatant was filtered with a filter, and the solubility was measured by the HPLC method.

The results are shown in Table 10.

TABLE 10

| CD or CD derivative |  | Solubility (mg/mL) |
|---|---|---|
| None |  | 0.2 |
| α CD | (NIHON SHOKUHIN KAKO CO., LTD.) | 30.2 |
| β CD | (NIHON SHOKUHIN KAKO CO., LTD.) | 5.9 |
| γ CD | (ASHLAND) | 14.4 |
| HP α CD | (NIHON SHOKUHIN KAKO CO., LTD.) | 25.7 |
| SBE β CD | (ChemScene) | 8.9 |
| 2,3,6-Tri-O-methyl-β-cyclodextrin | (Wako Pure Chemical Industries, Ltd.) | 4.7 |
| Hydroxyethyl-β-cyclodextrin | (Sigma-Aldrich) | 11.9 |
| HP β CD | (NIHON SHOKUHIN KAKO CO., LTD.) | 11.6 |
| DM β CD | (Sigma-Aldrich) | 16.6 |
| 6-O-α-maltosyl-β-cyclodextrin | (Wako Pure Chemical Industries, Ltd.) | 10.0 |
| Methyl-β-cyclodextrin | (Sigma-Aldrich) | 17.5 |
| HP γ CD | (ASHLAND) | 8.8 |

Compound A exhibited excellent solubility due to the CD or CD derivative.

INDUSTRIAL APPLICABILITY

The pharmaceutical composition comprising the hydroxamic acid derivative of the present invention or a salt thereof and a solubilizing agent exhibits a potent antimicrobial activity, has excellent solubility, and is useful as a medicine.

The invention claimed is:
1. A pharmaceutical composition comprising
(i) a hydroxamic acid derivative selected from the group consisting of: (2S)-2-((4-((4-((1S)-1,2-dihydroxyethyl)phenyl)ethynyl)benzoyl)(methyl)amino)-N-hydroxy-N',2-dimethylmalonamide, (2S)-2-((4-((4-((1R)-1,2-dihydroxyethyl)phenyl)ethynyl)benzoyl)(methyl)amino)-N-hydroxy-N',2-dimethylmalonamide, and (2S)-N-hydroxy-2-((4-((4-(1S)-1-hydroxy-2-methoxyethyl)phenyl)ethynyl)benzoyl)(methyl)amino)-N',2-dimethylmalonamide, or a salt thereof, and
(ii) at least one solubilizing agent selected from the group consisting of α-cyclodextrin, β-cyclodextrin, γ-cyclodextrin, hydroxypropyl-α-cyclodextrin, sulfobutylether-β-cyclodextrin, 2,3,6-tri-O-methyl-β-cyclodextrin, hydroxyethyl-β-cyclodextrin, hydroxypropyl-β-cyclodextrin, heptakis-2,6-di-O-methyl-β-cyclodextrin, 6-O-α-maltosyl-β-cyclodextrin, methyl-β-cyclodextrin, and hydroxypropyl-γ-cyclodextrin.

2. The pharmaceutical composition according to claim 1, wherein the hydroxamic acid derivative is (2S)-2-((4-((4-((1S)-1,2-dihydroxyethyl)phenyl)ethynyl)benzoyl)(methyl)amino)-N-hydroxy-N',2-dimethylmalonamide.

3. The pharmaceutical composition according to claim 1, wherein the solubilizing agent is one or more selected from the group consisting of α-cyclodextrin, γ-cyclodextrin, hydroxypropyl-α-cyclodextrin, sulfobutylether-β-cyclodextrin, hydroxyethyl-β-cyclodextrin, hydroxypropyl-β-cyclodextrin, heptakis-2,6-di-O-methvl-β-cyclodextrin, 6-O-α-maltosyl-β-cyclodextrin, and methyl-β-cyclodextrin.

4. The pharmaceutical composition according to claim 1, wherein the solubilizing agent is one or more selected from the group consisting of α-cyclodextrin, γ-cyclodextrin, hydroxypropyl-α-cyclodextrin, sulfobutylether-β-cyclodextrin, hydroxypropyl-β-cyclodextrin, and hydroxypropyl-γ-cyclodextrin.

5. The pharmaceutical composition according to claim 1, wherein the pharmaceutical composition is a liquid formulation.

6. The pharmaceutical composition according to claim 5, wherein a pH of the liquid formulation is from 3 to 8.

7. The pharmaceutical composition according to claim 1, wherein the pharmaceutical composition is a frozen liquid formulation.

8. The pharmaceutical composition according to claim 7, wherein a pH of the frozen liquid formulation when thawed is from 3 to 8.

9. The pharmaceutical composition according to claim 1, wherein the pharmaceutical composition is a lyophilized formulation.

10. The pharmaceutical composition according to claim 9, wherein a pH of an aqueous solution of the lyophilized formulation is from 3 to 8.

11. A method of inhibiting LpxC, comprising administering the pharmaceutical composition according to claim 1 to a subject in need thereof.

12. A method of inhibiting Gram-negative bacteria, comprising administering the pharmaceutical composition according to claim 1 to a subject in need thereof.

13. A method for producing a liquid formulation comprising a hydroxamic acid derivative or a salt thereof and a solubilizing agent, the method comprising:
dissolving the hydroxamic acid derivative selected from the group consisting of (2S)-2-((4-((4-((1S)-1,2-dihydroxyethyl)phenyl)ethynyl)benzoyl)(methyl)amino)-N-hydroxy-N',2-dimethylmalonamide, (2S)-2-((4-((4-((1R)-1,2-dihydroxyethyl)phenyl)ethynyl)benzoyl)(methyl)amino)-N-hydroxy-N',2-dimethylmalonamide, and (2S)-N-hydroxy-2-((4-((4-((1S)-1-hydroxy-2-methoxyethyl)phenyl)ethynyl)benzoyl)(methyl)amino)N',2-dimethylmalonamide, or the salt thereof, and the solubilizing agent in water to obtain an aqueous solution of the hydroxamic acid derivative or the salt thereof;
followed by adjusting a pH of the obtained aqueous solution to 3 to 8,
wherein the solubilizing agent is at least one selected from the group consisting of α-cyclodextrin, β-cyclodextrin, γ-cyclodextrin, hydroxypropyl-α-cyclodextrin, sulfobutylether-β-cyclodextrin, 2,3,6-tri-O-methyl-β-cyclodextrin, hydroxyethyl-β-cyclodextrin, hydroxypropyl-β-cyclodextrin, heptakis-2,6-di-O-methyl-β-cyclodextrin, 6-O-α-maltosyl-β-cyclodextrin, methyl-β-cyclodextrin, and hydroxypropyl-γ-cyclodextrin.

14. The production method according to claim 13, wherein the hydroxamic acid derivative is (2S)-2-((4-((4-((1S)-1,2-dihydroxyethyl)phenyl)ethynyl)benzoyl)(methyl)amino)-N-hydroxy-N',2-dimethylmalonamide.

15. The production method according to claim 13, wherein the solubilizing agent is one or more selected from the group consisting of α-cyclodextrin, γ-cyclodextrin, hydroxypropyl-α-cyclodextrin, sulfobutylether-β-cyclodextrin, hydroxyethyl-β-cyclodextrin, hydroxypropyl-β-cyclodextrin, heptakis-2,6-di-O-methyl-β-cyclodextrin, 6-O-α-maltosyl-β-cyclodextrin, and methyl-β-cyclodextrin.

16. The production method according to claim 13, wherein the solubilizing agent is one or more selected from the group consisting of α-cyclodextrin, γ-cyclodextrin, hydroxypropyl-α-cyclodextrin, sulfobutylether-β-cyclodextrin, hydroxypropyl-β-cyclodextrin, and hydroxypropyl-γ-cyclodextrin.

* * * * *